(12) United States Patent
Rabinovitz et al.

(10) Patent No.: US 8,523,788 B2
(45) Date of Patent: Sep. 3, 2013

(54) DEVICE, SYSTEM AND METHOD FOR EXAMINING A BODY LUMEN

(75) Inventors: Elisha Rabinovitz, Haifa (IL); Amit Pascal, Haifa (IL); Zvika Gilad, Haifa (IL); Daniel Afik, M.P. Misgav (IL)

(73) Assignee: Given Imaging Ltd., Yoqneam (IL)

( * ) Notice: Subject to any disclaimer, the term of this patent is extended or adjusted under 35 U.S.C. 154(b) by 303 days.

(21) Appl. No.: 12/850,904

(22) Filed: Aug. 5, 2010

(65) Prior Publication Data

US 2010/0305415 A1 Dec. 2, 2010

Related U.S. Application Data

(63) Continuation-in-part of application No. 10/988,614, filed on Nov. 16, 2004, now Pat. No. 7,585,283, which is a continuation-in-part of application No. 10/192,861, filed on Jul. 11, 2002, now Pat. No. 7,083,578.

(60) Provisional application No. 61/231,808, filed on Aug. 6, 2009.

(51) Int. Cl.
*A61B 5/117* (2006.01)
*A61B 5/103* (2006.01)

(52) U.S. Cl.
USPC .......................................... 600/593

(58) Field of Classification Search
USPC ................. 600/587, 593, 101, 160, 167, 178; 604/892.1, 890.1; 424/400, 451–453, 501, 424/426, 466, 78.37, 472, 457, 458, 465, 424/468, 470, 463, 464, 78.35; 521/99, 142, 521/149, 136, 134, 186, 189; 623/1.42
See application file for complete search history.

(56) References Cited

U.S. PATENT DOCUMENTS 6,346,269 B1 *  2/2002  Hsiao et al. .................... 424/472
6,599,284 B2 *  7/2003  Faour ........................ 604/892.1

(Continued)

FOREIGN PATENT DOCUMENTS

JP    2008-183237    8/2008
JP    2008-183239    8/2008
WO   WO 01/65995    9/2001

OTHER PUBLICATIONS

W. Weitschies, et al., High Resolution Monitoring of the Gastrointestinal Transport of a Magnetically Marked Capsule, Journal of Pharmaceutical Sciences, vol. 86, Issue 11, pp. 1218-1222, Nov. 1997.

(Continued)

*Primary Examiner* — Brian Szmal
(74) *Attorney, Agent, or Firm* — Pearl Cohen Zedek Latzer, LLP

(57) ABSTRACT

An in-vivo examining device, system and method for identifying the presence of strictures in the small bowel are provided. The in-vivo examining device includes a monitoring mechanism that becomes deactivated when exposed to in-vivo substances native to the small bowel or the colon, and a degradable device body that includes at least a first body portion which degrades at a slow rate when exposed to in-vivo substances native to the small bowel and at a fast rate when exposed to in-vivo substances native to the colon. The degradation of the degradable device body exposes the monitoring mechanism to substances native to the small bowel or the colon and thus indicates whether the examining device has safely passed through the small bowel or whether it is retained in the small bowel due to strictures in the small bowel.

20 Claims, 13 Drawing Sheets

(56) References Cited

U.S. PATENT DOCUMENTS

| | | |
|---|---|---|
| 7,009,634 B2 | 3/2006 | Iddan |
| 7,083,578 B2 | 8/2006 | Lewkowicz |
| 7,585,283 B2 | 9/2009 | Kraizer |
| 2005/0063906 A1 | 3/2005 | Kraizer et al. |

OTHER PUBLICATIONS

Hitachi, Ltd. Press Release, Operation verified on world's smallest 0.05 mm×0.05 mm "contactless powder IC chip". One-ninth the size of previous prototype, enabling, Feb. 13, 2007 (www.hitachi.com/rd/pdf/news/cr1070213nrde_RFID.pdf—no longer available), see http://www.hitachi.com/New/cnews/070213c.pdf.

Andreas Sieg, Is PillCam COLON Capsule Endoscopy Ready for Colorectal Cancer Screening ? A Prospective Feasibility Study in a Community Gastroenterology Practice, The American Journal of Gastroenterology, vol. 104, No. 4, pp. 848-854, Feb. 24, 2009.

Blair Lewis, Capsule Endoscopy—Transit Abnormalities, Gastrointest Endoscopy Clin N Am, vol. 16, No. 2, pp. 221-228, Apr. 2006.

Jonathan M. Buscaglia, et al., Enhanced Diagnostic Yield with Prolonged Small Bowel Transit Time during Capsule Endoscopy, International Journal of Medical Sciences, vol. 5, No. 6, pp. 303-308, Oct. 2008.

* cited by examiner

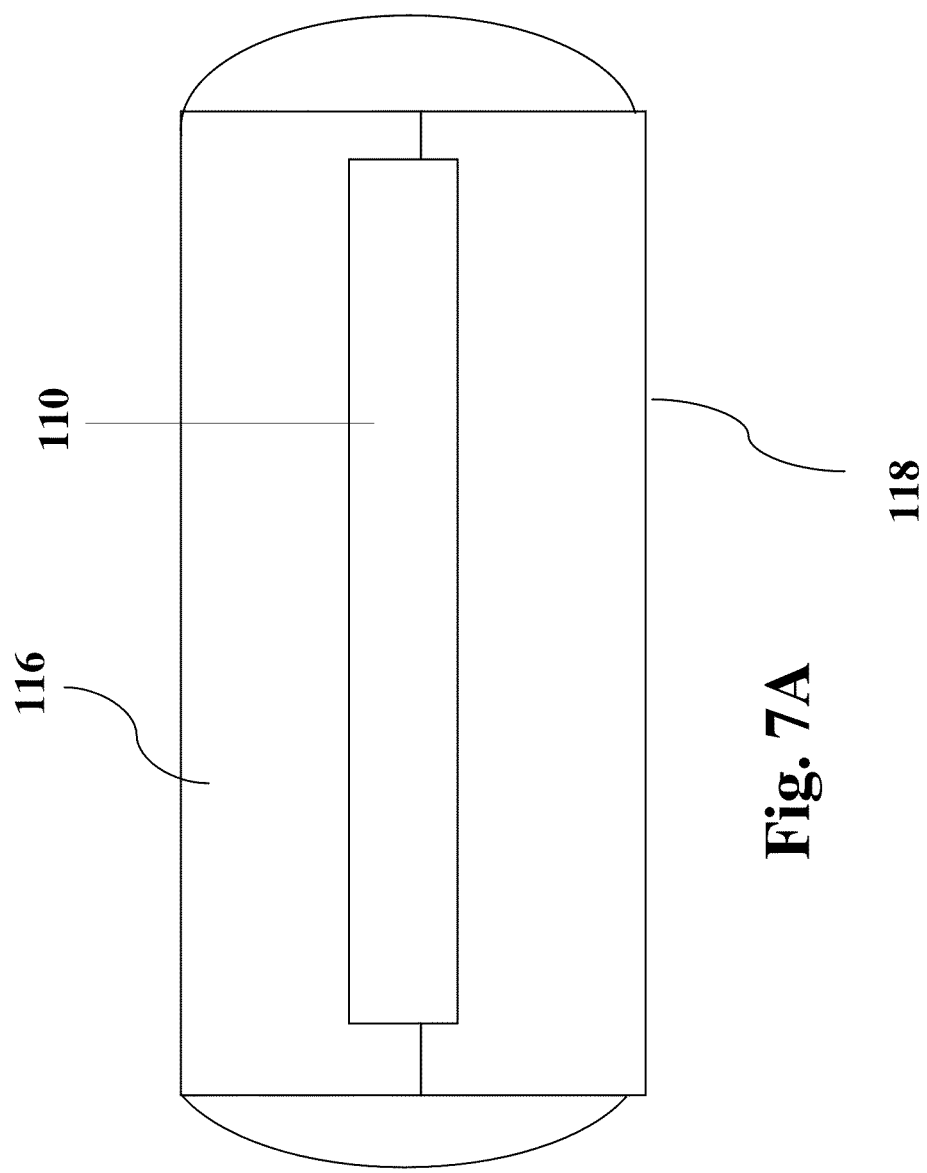

DEVICE, SYSTEM AND METHOD FOR EXAMINING A BODY LUMEN

CROSS-REFERENCE TO RELATED APPLICATIONS

This application claims the benefit of U.S. Provisional Patent Application No. 61/231,808 filed Aug. 6, 2009, which is incorporated by reference herein. This application is also a continuation-in-part of U.S. patent application Ser. No. 10/988,614, filed Nov. 16, 2004 now U.S. Pat. No. 7,585,283, entitled "Device and Method for Examining a Body Lumen", which in turn is a continuation-in-part of U.S. patent application Ser. No. 10/192,861, filed Jul. 11, 2002, entitled "Device and Method for Examining a Body Lumen", now U.S. Pat. No. 7,083,578, both of which are incorporated by reference herein in their entirety.

FIELD OF THE INVENTION

The present invention relates to a device, system and method for examining a body lumen using autonomous in-vivo medial devices. The device, system and method may be used to detect strictures within the gastrointestinal (GI) tract, specifically in the small bowel.

BACKGROUND OF THE INVENTION

Tubular organs in the body, such as the gastrointestinal (GI) tract, may have abnormalities, such as, strictures, narrowings or closures. These abnormalities may affect the anatomy or topology of the organs. Such abnormalities may be formed, for example, by calcification, scar tissue, tumors or other pathologies. Crohn disease, for example, which is typically a chronic inflammatory disease of the small bowel, may cause ulcers in the inner surface of the small bowel. In severe cases, large or deep ulcers may develop causing scarring and stiffness and possibly narrowing the small bowel. These abnormalities may obstruct the flow of material through the organs.

Methods for detecting abnormalities of the body lumen are often invasive, but some are non-invasive.

Some non-invasive methods for detecting abnormalities, specifically in the GI tract, include x-ray detection. In one method, x-ray opaque (radio-opaque) material (e.g., barium or gastrographine) may be ingested by a patient and a series of x-ray images that record the x-ray material in the body are captured. The material resides for some time on the walls of the GI tract, enabling examination of the x-ray images of the GI tract. This technique has several drawbacks, such as poor detection rate and patient exposure to x-ray radiation.

Other non-invasive techniques use solid non-degradable swallowable autonomous electronically or magnetically marked capsules. Electronically marked capsules may transmit electro-magnetic signals to a receiver external to the body to track the movement of the capsule through the GI tract. Magnetically marked capsules may alter the magnetic field, which may be measured to track the movement of the capsules in the GI tract. Magnetically marked capsule may be solid non-degradable capsules, e.g., containing powdered magnetite encapsulated in silicone rubber (W. Weitschies, R. Kotitz, D. Cardin, L. Trahms, (1997), *J Pharm Sci*, 86:1218-1222). Autonomous capsules may also be used to measure in-vivo conditions, such as gastric pH (e.g., using the Heidelberg capsule) and in-vivo temperature (e.g., using the Core-Temp™ capsule). Autonomous capsules are typically propelled through the GI tract by natural peristalsis. Autonomous capsules may monitor regions in the intestine, especially distal parts of the small intestine (e.g., the jejunum and ileum), that cannot be reached by other methods or devices. However, in cases where large strictures are located in narrow regions of the GI tract such as the small bowel, swallowing a solid bolus such as an autonomous capsule may itself cause an obstruction of the GI tract.

A method to determine if a stricture is large enough to prevent the safe passage of an autonomous medical device through the GI tract may include monitoring the passage of a test device resembling the medical device.

U.S. Pat. No. 7,083,578 describes passing a test device through the body. In one embodiment, the test device is an electronically marked autonomous capsule that transmits signals from inside the body to an external device outside of the body. If, after a period of time has elapsed, namely the predetermined period of time in which an unobstructed capsule should normally pass through the body, the external device may test whether or not the capsule is still transmitting signals from the body. If the external device receives no signals from the capsule, it may be determined that the capsule has been excreted from the patient's body. However, if the time period for the capsule passage has elapsed and the external device still receives signals, it may be determined that the capsule is stuck within the body lumen, for example, at the narrow passage of the small bowel.

Although the methods described in U.S. Pat. No. 7,083,578 may accurately determine if an autonomous device is stuck in a patient's body, this process has some drawbacks. For example, the time period in which an unobstructed capsule should typically stay in its initial dimensions is approximately thirty to a hundred hours. A patient is instructed to be on a liquid diet from noon of the first day. In the morning that follows, the patient may ingest the capsule. A practitioner would typically wait for thirty hours from the time the capsule was ingested by the patient to determine if the capsule is retained within the patient. After thirty hours, the practitioner may use an external scanner to scan the patient's abdomen and check signals are still emanating from the capsule. This amount of time prevents the use of imaging capsules shortly after test capsules.

Accordingly, there is a need in the art for a more efficient device, system and method to determine, within a relatively short period of time, if an autonomous device of a certain size and/or shape will pass safely through the GI tract, specifically through the small bowel.

SUMMARY OF THE INVENTION

Embodiments of the present invention provide a device, system and method for examining a body lumen using an autonomous in-vivo device. The autonomous in-vivo device may detect abnormalities in the gastrointestinal (GI) tract, including for example, stiffness and strictures due to Crohn's disease. Embodiments of the present invention provide a device, system and method for determining if an autonomous device of a certain size and/or shape will pass safely through the GI tract, e.g., in the region of the small bowel, within a short period of time. In some events, there may be narrowing in the small bowel, which may be viewed by Small Bowel Follow-Through Radiography (SBFT), while no real obstruction is present. In some events, a stricture may mistakenly be determined, while in fact a functional stricture is not present, i.e., the area where the narrowing is present can still function to push through substances during peristalsis. For example, a narrowing caused by an inflamed tissue may still be sufficiently flexible to enable passage of various substances (e.g., the device as follows), as opposed to when the tissue heals and thus becomes fibrotic and inflexible.

Therefore, embodiments of the present invention provide a device that distinguishes between apparent strictures in the small bowel and actual, functional strictures in the small bowel. Embodiments of the present invention provide a device that may determine whether there is functional patency (not just apparent patency), i.e., whether the tissue at the stricture is still sufficiently flexible to allow passage of the device and is thus still in a stage where medications may help or whether there is already an obstruction that may need a more serious intervention, e.g., surgery.

According to embodiments of the device, an in-vivo examining device to identify the presence of strictures in the small bowel may comprise a monitoring mechanism which becomes deactivated when exposed to in-vivo substances native to the small bowel or the colon. The device may further comprise a degradable device body comprising at least a first body portion which degrades at a first rate when exposed to in-vivo substances native to the small bowel and at a second rate when exposed to in-vivo substances native to the colon. According to some embodiments, the first rate is slower than the second rate. In some embodiments, degradation of the degradable device body exposes the monitoring mechanism to substances native to the small bowel or the colon.

In some embodiments, the device may comprise a substantially non-degradable or slowly-degradable coating surrounding the degradable device body, wherein the coating may comprise at least one opening. In some embodiments, the coating includes parylene C.

According to some embodiments, the monitoring mechanism is a radio-frequency identification (RFID) tag. The monitoring mechanism may be composed of a material selected from the group consisting of: paper, degradable plastic and degradable rubber. In some embodiments, the RFID tag may be rolled around itself within the device body. In other embodiments, the RFID tag may be wrapped around the device body and covered by the coating.

In some embodiments, the device body may comprise a filler disposed within the coating, the filler becoming dissolved in in-vivo fluids. In some embodiments, the device body may comprise a second body portion which degrades at a third rate when exposed to in-vivo substances native to the small bowel and at a fourth rate when exposed to in-vivo substances native to the colon, wherein the first rate is slower than the second rate. The first and second portions may be positioned at opposite sides along the longitudinal axis of the device.

According to embodiments of the present invention, an in-vivo examining device to identify the presence of strictures in the small bowel may comprise a monitoring mechanism, which is deactivated when exposed to in-vivo substances native to the small bowel or the colon, and a degradable device body comprising a first body portion which degrades at a first rate when exposed to in-vivo substances native to the small bowel and a second body portion which degrades at a second rate when exposed to in-vivo substances native to the colon. In some embodiments, the first rate is slower than the second rate. Degradation of the degradable device body exposes the monitoring mechanism to substances native to the small bowel or the colon, causing it to deactivate. In some embodiments, the first body portion and the second body portions are plugs positioned at opposite sides along the longitudinal axis of the device. In some embodiments, the first body portion may be comprised of a material chosen from the group consisting of: Compritol 888, Avicel PH 200, Lactose anhydr., PVP K-90 and/or a combination thereof. In some embodiments, the second body portion may be comprised of a material selected from the group consisting of: Crosslinked guar, a-Galactosidase, b-Mannanase, biodegradable polysaccharides, guar gum hydrogel, Trisodium trimetaphosophate, Pectin, Polysaccharide, Calcium pectinate and/or a combination thereof.

According to some embodiments, a method for determining the presence of a stricture in a small bowel may comprise the step of introducing into the small bowel a device that includes a dissolvable portion for dissolving in the colon at a first rate and for dissolving in the small bowel at a second slow rate. In some embodiments, the first rate is slower than the second rate. The device may further comprise a monitoring mechanism, and the device body may be covered by an impermeable coating defining at least two openings on opposite sides of the device body. In some embodiments, the method may comprise the step of monitoring the presence of a signal emanating from the monitoring mechanism, and the step of determining whether the device has passed through the small bowel or whether it is still present within the small bowel. In some embodiments, the step of introducing the device may comprise ingesting the device.

In some embodiments, the step of monitoring the device may comprise detecting a signal emanated from the monitoring device. In some embodiments, after the monitoring device is exposed to in-vivo fluids, the step of monitoring the device comprises detecting no signal emanated from the monitoring device.

In some embodiments, after a predetermined period, the device body and at least the dissolvable portion are dissolved, the predetermined time period may be a period of between 6 hours and 24 hours.

According to embodiments of the present invention, a system for determining the presence of strictures in the small bowel may comprise an examining device. The examining device may include first and second dissolvable portions for dissolving at a first rate in the small bowel and dissolving at a second rate in the colon, respectively. In some embodiments, the first rate is slower than the second rate. The device may further comprise a monitoring mechanism disposed between the first and second dissolvable portions. The device body may be covered by an impermeable coating defining at least two openings on opposite sides of the device body. In some embodiments, the system may further comprise a receiver for detecting a signal emanating from the monitoring mechanism after a predetermined time period to determine the presence of the examination device within the small bowel.

BRIEF DESCRIPTION OF THE INVENTION

The present invention will be understood and appreciated more fully from the following detailed description taken in conjunction with the appended drawings in which:

FIGS. 7A and 7B are schematic illustrations of cross-sectional views of an in-vivo examining device taken along a longitudinal axis and a lateral axis thereof, respectively, according to an embodiment of the present invention;

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

An atypical passage of an object through a body lumen or symptoms appearing after the insertion of an object into a body lumen may be indicative of an abnormal configuration of the body lumen. An examining device according to embodiments of the invention, which may, for example, examine a body lumen and/or may be an indicator of the body lumen configuration, may be designed to be depleted from its contents in-vivo and thus be safely excreted from the body, independently of the configuration of the body lumen. According to one embodiment, the body lumen may be the gastrointestinal (GI) tract.

Some components of device 100 of FIGS. 1 to 7B may become degraded, e.g., by exposure over time to in-vivo substances in a body lumen. However, in the views of FIGS. 1 to 7B these components are illustrated as intact components prior to degrading.

Figure 1:
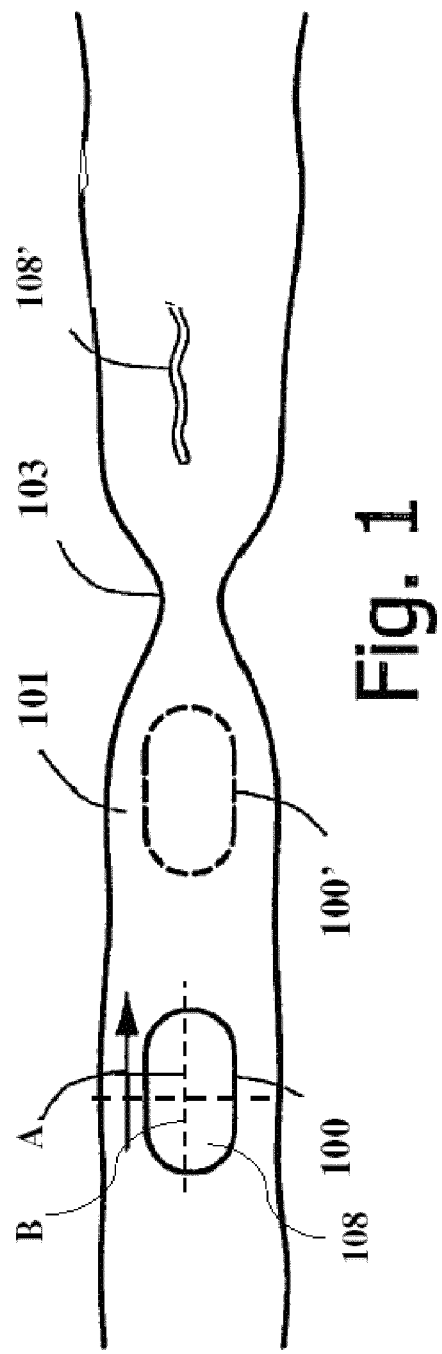
FIG. 1 is a schematic illustration of an in-vivo examining device traversing a body lumen according to an embodiment of the present invention.

Reference is made to FIG. 1, which schematically illustrates an in-vivo examining device 100 traversing a body lumen 101 according to an embodiment of the invention, Examining device 100 represents the device in a first position within body lumen 101, and examining device 100' represents the device in a second position that is farther advanced along body lumen 101, e.g., in a direction indicated by the arrow in FIG. 1. In some embodiments, device 100 may be used to detect abnormalities in body lumens, e.g., in the GI tract. Device 100 may be inserted into a patient's body by swallowing, by ingestion, or by being attached to another in-vivo device, e.g., to an endoscope or other device which may, for example, release device 100 inside the esophagus or anywhere else along the GI tract. Device 100 may move through body lumen 101 actively (e.g., by being pushed by an endoscope or other device) or passively (e.g., by natural peristalsis).

Device 100 may be passed through the GI tract, while its progression may be monitored within a predetermined time period from ingestion, to test the maneuverability of such a diagnostic or therapeutic imaging device through the GI tract. In the event that device 100 is retained in GI tract 101, e.g. in stricture 103, the shape or dimensions of device 100 may change to allow device 100 to pass through GI tract 101 in order to prevent obstruction thereof. However, if device 100 in its initial dimensions can be determined to have obstructed GI tract 101, a practitioner may be warned not to administer similarly shaped and sized autonomous medical devices that typically do not change shape.

Device 100 may be shaped, sized or have dimensions substantially similar to another, autonomous ingestible imaging device that may be used for imaging the GI tract. Device 100 may be, for example, a capsule shaped similarly to ingestible capsules described in U.S. Pat. No. 7,009,634 entitled "Device for In Vivo Imaging," and/or International Publication Application Number WO/2001/65995 "A Device and System for In Vivo Imaging", each of which are incorporated herein by reference, and/or to the PillCam® Small Bowel capsule endoscopes of the common assignee of the present invention. In one example, device 100 may be shaped as a capsule having initial dimensions of approximately 11 to 13 millimeters (mm) in width and 26 to 32 mm in length. Alternatively, device 100 may be shaped and/or sized similarly to any pill, tablet, capsule or other in-vivo device known in the art for the purpose of predicting the success of the passage of that device, e.g. the Agile™ patency capsule by Given Imaging Ltd.

Device 100 may have initial dimensions similar to the dimensions of an in-vivo imaging device that is intended to be ingested by a patient after determining patency of the small bowel within a predetermined time period. For example, device 100 may have initial dimensions including a diameter of approximately 11-13 mm, which corresponds for example to the PillCam® Small Bowel capsule endoscopes. In other embodiments, where an in-vivo sensing device to be taken subsequent to device 100 is of a smaller diameter than 11-13 mm, device 100 may also be of a smaller diameter, accordingly.

The opening of body lumen 101 (e.g., the GI tract) may have a diameter, for example, varying from approximately 20 mm to 5 cm along the length thereof. For example, the esophagus and the small bowel are approximately 25 mm in diameter and the colon is approximately 50 mm in diameter. According to these dimensions or dimensions proportional thereto, device 100 may pass freely through body lumen 101. Alternatively, device 100 may pass through other body lumens and may have other suitable initial dimensions. At and/or near a stricture 103, as shown in FIG. 1, the diameter of the opening of body lumen 101 may be less than or equal to the diameter of device 100. For example, stricture 103 may have a diameter of approximately 2-15 mm. Device 100' at an advanced position (illustrated using a broken line) may be unable to continue its passage through the body lumen 101 when its dimensions are larger than the dimensions of the opening of body lumen 101 at stricture 103. Device 100, in its initial dimensions, may thus be blocked at the stricture 103 and may obstruct the opening of body lumen 101 at stricture 103. Prolonged obstruction of body lumen 101 may be dangerous and/or uncomfortable for a patient.

In order to determine whether or not device 100 having its initial dimensions will pass substantially unobstructed through body lumen 101 (e.g., the GI tract), it may be sufficient to determine whether or not device 100 will pass substantially unobstructed through a region of body lumen 101 having the narrowest opening. When the body lumen 101 of interest is the gastrointestinal tract, the region having the narrowest opening is the small bowel. For example, if device 100 moves unobstructed through the small bowel, then it may be expected to move unobstructed through the remaining regions in GI tract 101, e.g., the esophagus, the stomach, the colon, etc. each of which is relatively wider than the small bowel. Accordingly, it may be sufficient only to the behavior of device 100 to ensure that it completely passes through the small bowel and enters the adjacent organ, i.e., the colon.

The time it typically takes an in-vivo device, such as an endoscopy capsule, to traverse the esophagus is a few seconds, when swallowed by a patient in an upright position. The typical transit time of an in-vivo device in the stomach is between a few minutes to one hour. (see "Capsule endoscopy-Transit abnormalities" by Lewis B. in *GI Endoscopy Clinics of North America*). The typical transit time of an in-vivo device in the small bowel is 2-8 hours (see "Enhanced Diagnostic Yield with Prolonged Small Bowel Transit Time During Capsule Endoscopy" by Buscaglia et al. in *International Journal of Medical Sciences*). Transit time in the colon is a few to several hours, typically around 6 hours (see "Is Pillcam Colon Capule Endoscopy ready for Colorectal Cancer Screening? A Prospective Feasibility Study in a Community Gastroenterology Practice" by Sieg et al. in *The American Journal of Gastroenterology*). The time when device 100 is expected to exit the small bowel and enter the colon is a critical time period, e.g., typically between 4 to 12 hours after ingestion, if device 100 is unobstructed, i.e., a few seconds to pass the esophagus, a few minutes to pass the stomach and a few hours to traverse the small bowel.

Embodiments of the invention provide a device, system, and method for determining if, at this critical time period, device 100 has entered the colon or is stuck in the small bowel. Such embodiments provide an advantage over the aforementioned methods in which the safe passage of the device may be determined only after complete passage of a device through the body (e.g., after 100 hours). Embodiments of the invention provide a device that dissolves or at least begins to dissolve within a short period of time (e.g., within 1-4 hours) after entering the colon, while dissolving within an extended period of time (e.g., within 40 hours) when in the small bowel.

According to some embodiments, a method of examination using device 100 may include, on a first day, a patient swallowing device 100 and, on the next day (e.g., after 13 hours), a practitioner determining whether device 100 has safely passed through the small bowel or whether device 100 is retained within the small bowel. Since the time from the time of ingestion that device 100 is expected to reach the colon, when unobstructed, is normally between 4-12 hours, a practitioner may determine after 13 hours, for example, whether device 100 is retained within the small bowel or whether it has passed through the small bowel and reached the colon. If the practitioner has determined that device 100 has reached the colon within, e.g., 13 hours, then the patient may be safely administered an imaging capsule having the same dimensions or smaller as the initial dimension of device 100, soon after the practitioner's positive diagnosis.

The duration of an unobstructed passage of device 100 through the small bowel until it enters the colon is between 4-12 hours, and, according to embodiments of the present invention, degradation of device 100 in the colon is designed to begin within 1 hour from entering the colon. Thus, "degradation time of an unobstructed passage" of device 100 in the GI tract is up to 13 hours. However, "degradation time of an obstructed passage" would typically last longer than 13 hours. That is, a physician may determine within, e.g., 13 hours whether device 100 has safely reached the colon or whether it is retained in the small bowel due to, for example, strictures in the small bowel.

Figure 2:
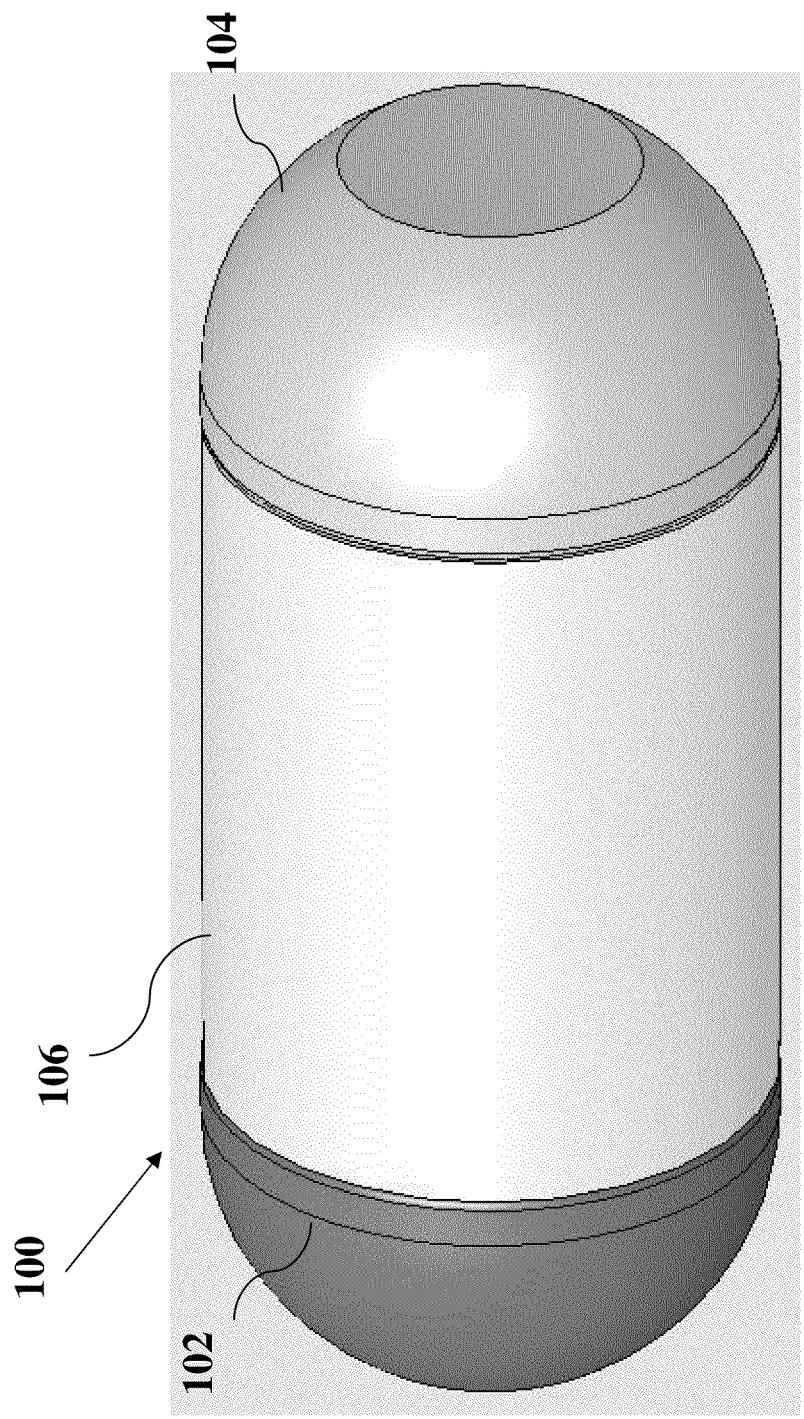
FIG. 2 is a schematic illustration of a perspective view of the examining device according to an embodiment of the present invention.

Reference is made to FIG. 2, which schematically illustrates a perspective view of examining device 100 according to an embodiment of the present invention. Device 100 may include a device body 106 and two or more plugs 102 and 104 attached to the device body 106. These components may be encapsulated by coating 108 (shown in FIG. 3), although no coating 108 is illustrated in FIG. 2 so as not to obscure the view of the components.

Figure 3:
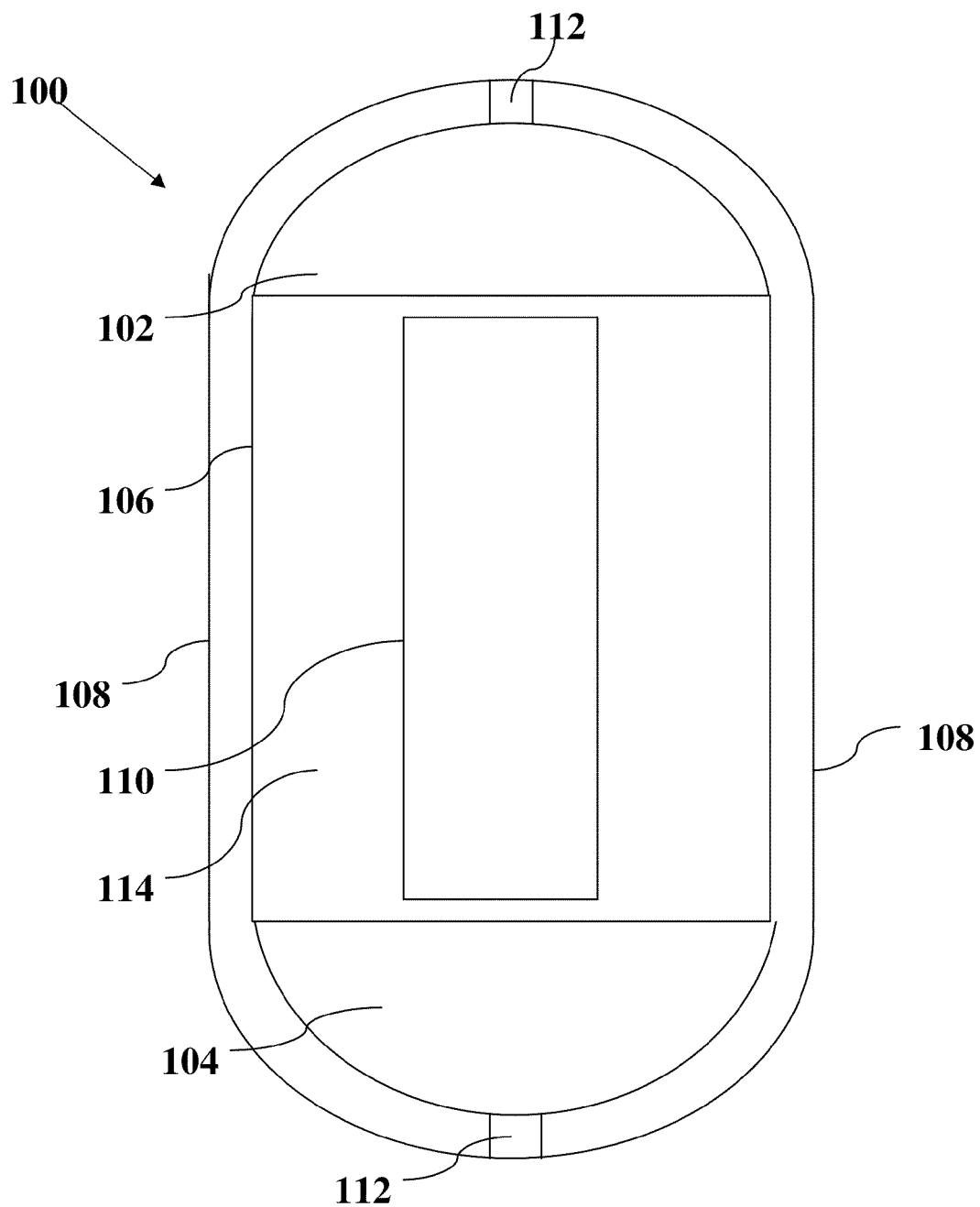
FIG. 3 is a schematic illustration of a cross sectional view of the examining device of FIG. 2 taken along a longitudinal axis thereof, according to an embodiment of the present invention.

Reference is now made to FIG. 3, which is a schematic illustration of a cross sectional view of examining device 100 of FIG. 1 taken along a longitudinal axis thereof, according to an embodiment of the present invention. Device 100 may include a device body 106 and two or more plugs 102 and 104 attached to the device body 106. Plugs 102 and 104 and device body 106 encapsulate a monitoring mechanism 110 that enables monitoring of the progress of device 100 through the body lumen 101. Device 100 may optionally include an outside covering or coating 108 having one or more openings 112. According to some embodiments, coating 108 may be made of a thin layer of impermeable polymer, for example, a thin layer of Parylene C, for example, an 8-10 µm layer of Parylene C. Other suitable coatings and coating methods may be used.

A first plug 102 may be attached to a first end of device body 106, and a second plug 104 may be attached to a second end of device body 106. Typically, plugs 102 and 104 are attached at opposite ends of device body 106, although they may be located anywhere in device 100. Plugs 102 and 104 may be attached to device body 106 for example via a joint, plug, press process or locking mechanism. Plugs 102 and 104 may be glued to device body 106 with an adhesive, for example, a biocompatible adhesive, e.g., UV glue such as DYMAX MD® "1000" Series Medical Device adhesives manufactured by DYMAX®. In other examples, plugs 102 and 104 may be affixed to device body 106 by packaging and/or coating, such as coating 108. Other suitable methods of joining plugs 102 and 104 to device body 106 may be used.

Plugs 102 and 104 and monitoring mechanism 110 are typically composed of degradable materials. Device body 106 is preferably, but not necessarily, composed of degradable materials. Degradable materials include, for example, any material that erodes, dissolves, unwinds, collapses or otherwise decreases in one or more dimensions under normal conditions of use (e.g., while traversing the body lumen) within a predetermined amount of time (e.g., the time of passage through the lumen).

Each of plugs 102 and 104 may be composed of different degradable materials. Each different degradable material may have a different rate of degradation that depends on the in-vivo substances (e.g., fluids, enzymes, bacteria, etc.) associated with different regions of body lumen 101 in which device 100 may be located. For example, plug 102 may be composed of a material that degrades when exposed to in-vivo substances native to the small bowel, while plug 104 may be composed of a material that degrades when exposed to in-vivo substances native to the colon. Plug 102 may be composed of, for example, Compritol 888® (Glyceryl dibehenate), Avicel PH 200® (microcrystalline cellulose), Lactose anhydr., PVP K-90, or a combination thereof. Plug 104 may be composed of, for example, Crosslinked guar, a-Galactosidase, b-Mannanase, biodegradable polysaccharides, guar gum hydrogel, Trisodium trimetaphosophate, Pectin, Polysaccharide, Calcium pectinate or a combination thereof. Other materials may also be used.

According to some embodiments, plugs 102 and 104 may be composed of the same material that dissolves slowly when exposed to in-vivo substances native to the small bowel, while dissolving quickly when exposed to in-vivo substances native to the colon. For example, plugs 102 and 104 may be composed of a combination of the above mentioned materials that degrade in the colon and of the mentioned materials that degrade in the small bowel, so as to control the different degradation rates according to the location in-vivo of device 100. In some embodiments, for example, plugs 102 and 104, which are composed of the same material, may dissolve or degrade in the colon within 1 hour from entering the colon, and may dissolve or degrade in the small bowel within 40 hours from entering the small bowel. In other embodiments, plugs 102 and 104 may begin to dissolve within 1 hour from entering the colon such that at least monitoring mechanism 110 may be deactivated within that hour, thus indicating on safe passage of device 100 through the small bowel.

Monitoring mechanism 110 may transmit signals from within device 100 to an external receiver device, for example, a radio frequency scanner (not shown). Monitoring mechanism 110 may be enclosed or protected by degradable material (e.g., device body 106 and plugs 102 and 104) and may itself be composed of a degradable material. When one or both of plugs 102 and 104 degrade, monitoring mechanism 110 may become exposed to in-vivo fluids and will degrade and become deactivated (i.e., stop transmitting identification signals). When plugs 102 and 104 degrade at different rates based on the region of body lumen 101 in which device 100 is located, depending on which plug 102 or 104 degrades first, monitoring mechanism 110 is exposed and thereby inactivated at corresponding different times. Accordingly, the presence or absence of a signal from monitoring mechanism 110 at one of the corresponding different times may indicate the region of body lumen 101 in which device 100 is located.

Monitoring mechanism 110 may be, for example, an identification (ID) tag, e.g., a degradable radioactive, chemical, color or magnetic tag or an electronic ID tag. Monitoring mechanism 110 may be, for example, a radio-frequency (RF) ID tag, which may be printed on paper, degradable rubber, degradable plastic or any other degradable material, e.g., chipless RFID tags such as SARcode™ Development by InkSure Technologies. In other embodiments, the RFID tag need not be degradable or semi-degradable but rather may be made of a non-degradable material with or without a waterproof case. According to some embodiments, the RFID tag may be the TROVAN ID-100A Microtransponder, HUA-YUAN by Shanghai Huayuan Electronic Co. Ltd or Glass Tag by Sunbest Technology Company Ltd. The ID tag may include a decodable pattern imprinted using a conductive ink composed of, e.g., a pure metal, such as silver or a metal alloy. Monitoring mechanism 110 typically transmits signals passively by reflecting energy from the external receiver device, e.g., an RF scanner, to send back an identification signal corresponding to the printed pattern of the RF ID tag. The external receiver device may include, e.g., an ohmmeter, milliohm meter, RF network analyzer, impedance-measuring equipment, etc., capable of identifying and decoding identification signals received from monitoring mechanism 110.

In one embodiment of the invention, device body 106 may be composed of a degradable material 114. Alternatively, device body 106 may be composed of a non-degradable material, as long as degradable plugs 102 and 104 or another degradable material is in contact with monitoring mechanism 110. Degradable material 114 may include, for example, biodegradable or dissolvable material, for example any suitable excipient, e.g., lactose, powdered sugar, etc. In some embodiments, degradable material 114 may be made of the same material as plugs 102 and 104 are made of, e.g. a material that dissolves quickly in the colon and slowly in the small bowel. Typically, degradable material 114 may be strong enough to withstand endo-luminal pressure. Degradable material 114 may also contain adhesives and fillers to, for example, further provide mechanical stability to the device. Degradable material 114 may optionally include x-ray opaque material, e.g., barium sulphate powder, for monitoring device 100 using x-ray techniques. Other suitable materials may be used. Degradable material 114 may be pressed into a desired shape and dimensions by known methods to form device body 106. In one embodiment of the present invention, degradable material 114 may be cylindrical with dimensions approximating 12-14 mm in length and 9-12 mm in diameter. Other suitable dimensions may also be used.

In one embodiment, device 100 may include an outer coating 108. Coating 108 may be substantially non-degradable or may degrade at a relatively slow rate compared to other components of device 100. Coating 108 may cover the degradable components of device 100 and reduce their exposure to in-vivo fluids to retard the degrading of device 100 until it has progressed to the appropriate in-vivo location. Coating 108 may be sufficiently rigid and stable to ensure that device 100 substantially maintains its initial dimensions of width for at least the period of time for determining if device 100 has passed unobstructed to the colon, i.e. "degradation time of an unobstructed passage" (e.g., up to 13-24 hours in the example below). After that time period, the interior of device 100 may continue to degrade, e.g., until it mostly or completely degrades, at which point coating 108 collapses so that device 100 has a smaller dimension of width. Therefore, if after it is determined that device 100 in its initial dimensions of width is stuck in the small bowel, device 100 may collapse to prevent continued obstruction of body lumen 101.

Coating 108 may completely encapsulate the contents of device 100 except at one or more openings 112. Openings 112 preferably align with each of plugs 102 and 104, although they may be located anywhere along coating 108. Opening 112 may regulate the flow of in-vivo fluids therethrough so as to control or retard the exposure of degradable components of device 100 to the in vivo fluids. In one embodiment, openings 112 are non-degradable, e.g., they are simply holes formed through non-degradable coating 108.

In an alternative embodiment, the openings 112 may themselves be separate degradable structures (e.g., rings or cylinders) that are fit into an opening or holes formed through non-degradable coating 108. In this embodiment, before degrading, openings 112 may have initial shapes and sizes with or without holes formed therethrough. Degradable openings 112 may degrade when device 100 is at the appropriate in-vivo location, for example, by being composed of materials with specific degrade rates or that are activated by in-vivo material that is found only or predominantly in the appropriate in-vivo location. In one embodiment, each opening 112 may be composed of the same material as the one of plugs 102 and 104 that is covered by the opening 112. In this embodiment, the rate of degradation of adjacent plugs 102 and 104 and openings 112 may coincide.

In one embodiment, the entire contents of device 100 may be substantially degradable except, for example, outside coating 108. In one embodiment, relative to the rate at which components of device 100 degrade, capsule coating 108 may have the slowest rate of degrading or may not degrade at all, and monitoring mechanism 110 may have the fastest rate of degrading (e.g., instantly when exposed to or saturated by liquids).

In an alternative embodiment, device 100 may have no outside coating 108. In such embodiments, device 100 may be guided by an endoscope to the appropriate in-vivo location so as to prevent premature exposure of degradable components of device 100 to in-vivo substances.

In another embodiment, degradation of device 100 may be initiated on demand, e.g., by an RF signal sent from outside the patient's body. In some embodiments, once a practitioner determines that device 100 is retained in the small bowel such that it may obstruct an opening of the small bowel, the practitioner may initiate degradation of the device by sending a signal through RF to monitoring mechanism 101 that will cause the device 100 to dissolve. For example, the RF signal may cause either one or both of openings 112 to open such that plugs 102 and 104 may be exposed to in-vivo fluids and thus begin to dissolve. During and after dissolving of plugs 102 and/or 104 degradable material 114 may also begin to degrade thereby causing device 100 to acquire smaller dimensions than its initial dimensions and thus enable device 100 to freely pass through the rest of the small bowel.

Device 100 may include, for example, two phases of degradation. In the first phase, plugs 102 and 104 degrade, which may alter or reduce some dimensions of device 100 (in the longitudinal axis of device 100), but preferably do not alter the outer dimension of width or girth of device 100 (perpendicular to the longitudinal axis). This first phase includes the degradation of plugs 102 and 104 at different rates based on the region of body lumen 101 in which device 100 is located. This selective degrading enables the monitoring mechanism 110 to be exposed to in vivo fluids and to be thereby deactivated at corresponding times, so as to indicate the region of body lumen 101 in which device 100 is located.

According to some embodiments, coating 108 may be composed of a non-degradable material with sufficient rigidity to maintain the dimensional width or girth of device 100 (e.g., matching the width or girth of a non-degradable medical device) until monitoring mechanism 110 is exposed and it is determined whether or not a device of such width is able to pass unobstructed through body lumen 101. Once this is determined, it may no longer be necessary to preserve the dimension of width of device 100.

Accordingly, in the second phase of degrading, device 100 may be reduced in the dimension of width or girth. After one or more of plugs 102 and 104 are at least partially degraded, a passageway is formed through openings 112 of coating 108 through which in-vivo material may flow and continue to degrade device body 106. Once a sufficient amount of device body 106 is degraded, coating 108 may collapse and the dimension of width or girth of device 100 is thereby reduced. This second phase of degrading may act as a safety mechanism to allow device 100 to pass through openings of body lumen 101 that are too narrow for device 100 to pass through when device 100 has its initial dimensions.

It may be appreciated that the first and second phases of degrading may be simultaneous, overlapping or non-distinct. However, the first phase of degrading typically proceeds or at least begins before the second phase begins. Furthermore, in order to determine whether a subsequent non-degradable medical device will safely pass the small bowel unobstructed, it is preferable for device 100, which tests the passage, to have substantially the same dimension of width or girth as the non-degradable medical device. Accordingly, the second phase, in which the dimension of width or girth of device 100 is reduced, may only begin after a critical time for determining such passage. For example, in order to prolong the second phase of degrading, interior components of device 100, e.g., device body 106, may be composed of a material with a rate of degrading that is small enough to ensure that device 100 does not collapse before a critical time period has lapsed.

In one embodiment, as discussed above, plugs 102 and 104 may being to degrade at different times corresponding to exposure to in-vivo substances in different regions of body lumen 101. When either of plugs 102 and 104 degrades, monitoring mechanism 110 is exposed to in-vivo fluids and will stop transmitting identification signals. By scanning for the presence or absence of signals from monitoring mechanism 110 at the different times, a practitioner may determine which of plugs 102 and 104 has degraded and, therefore, may determine where, i.e., in which region of body lumen 101, device 100 is located.

In one embodiment, relative to the rate that plug 104 degrades, plug 102 may degrade at a rate that is faster when exposed to in-vivo substances in the small bowel and at a rate that is slower when exposed to in-vivo substances in the colon. Accordingly, relative to the rate that plug 102 degrades, plug 104 may degrade at a rate that is faster when exposed to in-vivo substances in the colon and at a rate that is slower when exposed to in-vivo substances in the small bowel.

In another embodiment, plugs 102 and 104 may be made of the same material and thus degrade at the same rate according to the different regions of the GI tract. In such an embodiment, plugs 102 and 104 may both degrade slowly in the small bowel (e.g., within 40 hours from entering the small bowel) and may both degrade quickly in the colon (e.g., within 1-4 hours from entering the colon). This embodiment ensures exposure of monitoring mechanism 110 to in-vivo fluids from either one of the ends of device 100. For example, if device 100 encounters a stricture such that one of its ends/plugs is no longer in contact with in-vivo fluids, the other plug (typically opposite the plug retained at the stricture), which is in contact with in-vivo fluids, will begin to degrade.

According to some embodiments, monitoring mechanism 110 may be exposed to in-vivo fluids of the colon or of the small bowel before either of the plugs has entirely dissolved, since any amount of in-vivo fluids that monitoring mechanism 110 is exposed to may deactivate it. For example, monitoring mechanism 110 may stop transmitting identification signals within 1 hour from entering the colon even though the plug through which in-vivo fluids have entered is not completely dissolved. This may give an early indication as to whether or not device 100 has safely reached the colon and whether or not the patient may administer an imaging capsule of the same dimensions as the initial dimensions of device 100.

In one embodiment, in the small bowel, plug 102 may degrade by an amount sufficient to expose monitoring mechanism 110 to the substances in the small bowel and thereby deactivate the device after a first predetermined time period of exposure, e.g., 24 hours. Typically, plug 104 may degrade in the small bowel after a second predetermined time period of exposure, e.g., 50 hours, which is larger than the first time period. In one embodiment, in the colon, plug 104 may degrade by an amount sufficient to expose monitoring mechanism 110 to the substances in the colon and thereby inactivate the device after a third predetermined time period of exposure, e.g., 1 hour. Typically, plug 102 may degrade in the colon after a fourth predetermined time period, e.g., 10 hours, which is larger than the third time period. In other embodiments, plugs 102 and 104 may be made of the same material that may degrade in the small bowel after a fifth predetermined time period of exposure, e.g., between 24 to 50 hours, and may degrade in the colon after a sixth predetermined time period of exposure, e.g., between 1 to 4 hours.

Under normal, unobstructed conditions, device 100 is expected to pass through the small bowel and enter the colon after a predetermined time period, e.g., approximately 4-12 hours, as described above. This predetermined time period is too short for either of plugs 102 and 104 to degrade while in the small bowel by an amount sufficient to inactivate monitoring mechanism 110 (i.e., plugs 102 and 104 require first and second time periods to sufficiently degrade in the small bowel, 24 and 50 hours, respectively). Once the unobstructed device 100 passes to the colon, after an additional time period in the colon (e.g., the third time period, e.g., of 1 hour to provide a total of up to 13 hours), plug 104 will degrade, exposing monitoring mechanism 110 to the substances in the colon and thereby inactivating monitoring mechanism 110. Accordingly, if an external device receives no signals from monitoring mechanism 110 after "degradation time of an unobstructed passage", it may be determined that device 100 has passed unobstructed through the small bowel and into the colon. The unobstructed time period may be (e.g., 13 hours), for example, the sum of the predetermined time period in which an unobstructed device 1.00 is expected to pass through the small bowel and enter the colon (e.g., 12 hours) and the third time period in which plug 104 is expected to degrade within the colon (e.g., 1 hour). If, however, an external device continues to receive signals from monitoring mechanism 110 after the unobstructed time period, it may be inferred that device 100 is retained in the small bowel and has not progressed to the colon in the time expected for an unobstructed device.

In this way, the "degradation time of an unobstructed passage" (e.g., 13 hours in the above example) is a critical time period, after which it may be determined whether or not device 100 has progressed through the small bowel and into the colon substantially unobstructed (i.e., if no signals are transmitted) or alternatively, if device 100 is stuck in the small bowel (i.e., if signals continue to be transmitted).

If device 100 is stuck in the small bowel, monitoring mechanism 110 will continue to transmit signals up to a predetermined "degradation time of an obstructed passage" (e.g., 24 hours from ingestion), after which plug 102 will be degraded and monitoring mechanism 110 will be deactivated. Once plug 102 is degraded, in its absence there is a passageway through openings 112 of coating 108 through which in-vivo material may degrade the remainder of the insides of device 100, such as device body 106. Once a sufficient amount material of the interior of device 100 has been degraded, coating 108 will collapse so that device 100 will have a significantly smaller dimension of width or girth (i.e., the second phase of degrading). The narrower device 100 may then pass through the previously obstructive passage of the small bowel to prevent continued obstruction of body lumen 101.

If, after the critical unobstructed time period, one or more signals are continued to be received from monitoring mechanism 110, a practitioner may conclude that it is unsafe to administer a non-degradable device of similar shape and size to the patient. Alternatively, the practitioner may continue testing, periodically or continually scanning the patient after the unobstructed time period to determine when and if device 100 passes to the colon with its initial dimension of width. That is, if signals stop before the obstructed time period (e.g., at 14 or 15 hours after ingestion), it may be determined that this time lag from the unobstructed time period indicates that there is a serious obstruction, that there is a minor obstruction, or, alternatively, that the time lag corresponds to a margin of error attributed to relatively slow peristalsis rate of the patient. The practitioner may, at his/her discretion, decide whether or not it is safe for a similarly shaped and sized medical device to be administered to the patient for passage through body lumen 101.

As described above, since the small bowel is narrower than any openings downstream within body lumen 101, in order to determine that device 100 has progressed to the colon substantially unobstructed by the small bowel, it may be sufficient to determine whether or not device 100 will pass substantially unobstructed through the remainder of body lumen 101. In contrast to other methods and devices, which as described may take over 100 hours to determine if there is an obstruction of the lumen, in one embodiment of the invention, an obstruction may be determined within a critical period of, for example, 13 hours after the ingestion of device 100 into a patient's body.

Accordingly, a practitioner may administer device 100 to a patient one day, and the next day (e.g., after 13 hours) may scan monitoring mechanism 110, e.g., using a RF scanner, to determine if device 100 has passed unobstructed to the colon. If the practitioner cannot detect a signal from device 100, the practitioner may administer to the patient a second device of similar size and shape and composed of non-degradable material, e.g., an imaging capsule for imaging the GI tract. Since it typically takes up to 100 hours for device 100 to completely pass through a patient's body but it takes only approximately 13 hours to determine whether it is safe to administer a second non-degradable device to the patient, both devices may traverse through a patient's body at once. There should be substantially no interference between signals from device 100 and signals from the second non-degradable device because the second non-degradable device is typically ingested only after it has been determined that no signals are received from monitoring mechanism 110 (i.e., so as to ensure that device 100 has safely passed the small bowel).

The exact times and rates of degradation of materials in device 100 may depend on the material(s) from which the plugs 102 and 104, are composed and the substances present in the region of body lumen 101, which may differ, e.g., between individuals, based on diet and/or time of day. The aforementioned time periods described are demonstrative examples and different time periods may equivalently be used.

In an alternate embodiment, exposure of monitoring mechanism 110 to in-vivo fluids does not deactivate monitoring mechanism 110, but rather only alters its signals. For example, in one embodiment, monitoring mechanism 110 may include both a paper RFID tag that is deactivated when exposed to in-vivo fluids and a metal RFID tag that is unaffected by in-vivo fluids (or an RFID tag that is encapsulated in a container, e.g., glass cover that is water insoluble). Accordingly, when one of plugs 102 and 104 degrades and monitoring mechanism 110 is thus exposed to in-vivo fluids, only paper RFID tag and not metal RFID tag (or encapsulated RFID tag) will be deactivated. The metal (or encapsulated) RFID tag may be used to determine when or whether device 100 has been excreted from the patient's body. When no signals are transmitted by the metal (or encapsulated) RFID tag, then it may be determined that device 100 is no longer within the patient's body.

In another embodiment, monitoring mechanism 110 may include a paper RFID tag that is partially encapsulated by a water insoluble cover or coating. Accordingly, when one of plugs 102 and 104 degrades, only a portion of the paper RFID tag may be deactivated so that the signals therefrom will continue, albeit with an altered code or identification.

Figure 4A:
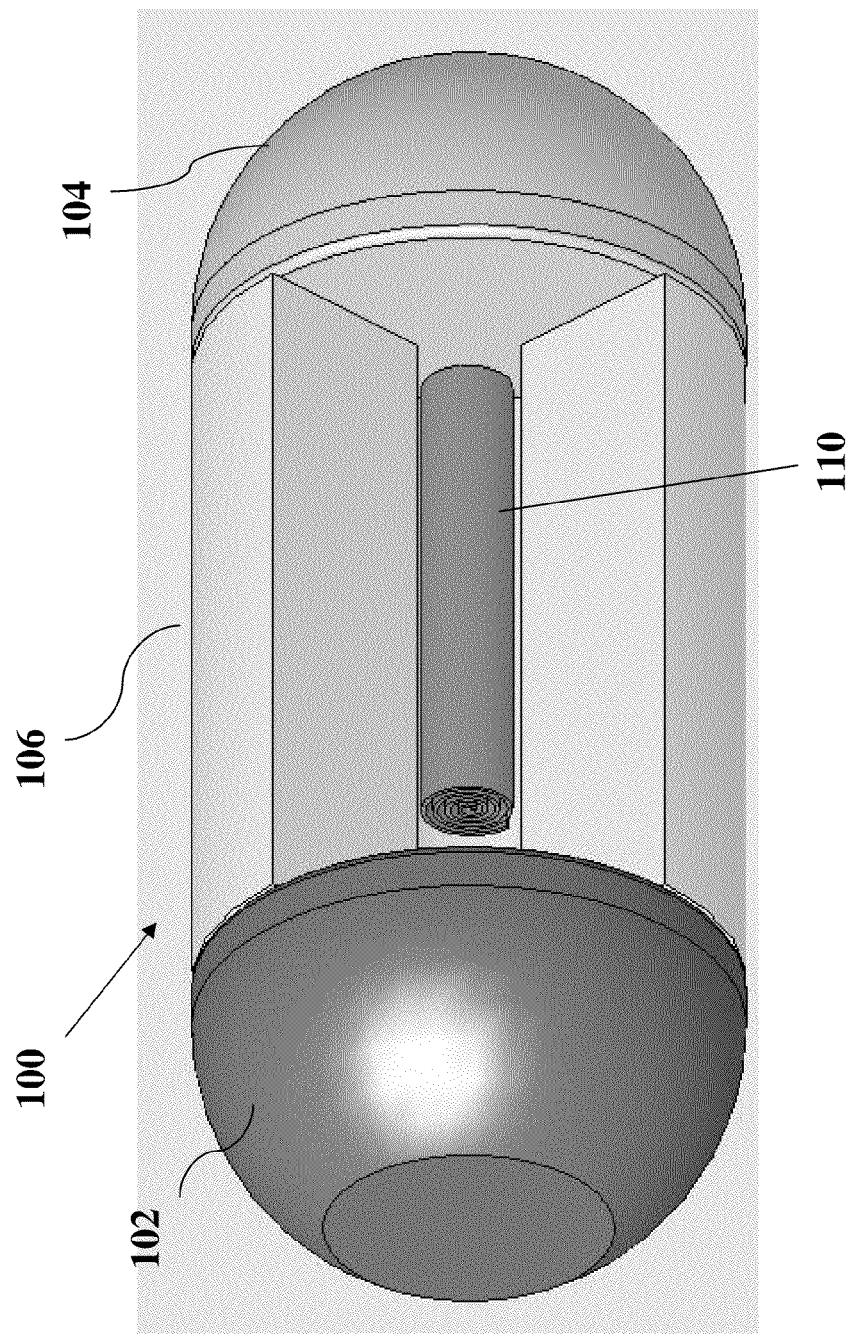
FIGS. 4A and 4B are schematic illustrations of a partially sectioned perspective view and a cross-sectional view, respectively, of the examining device according to an embodiment of the present invention.
Figure 4B:
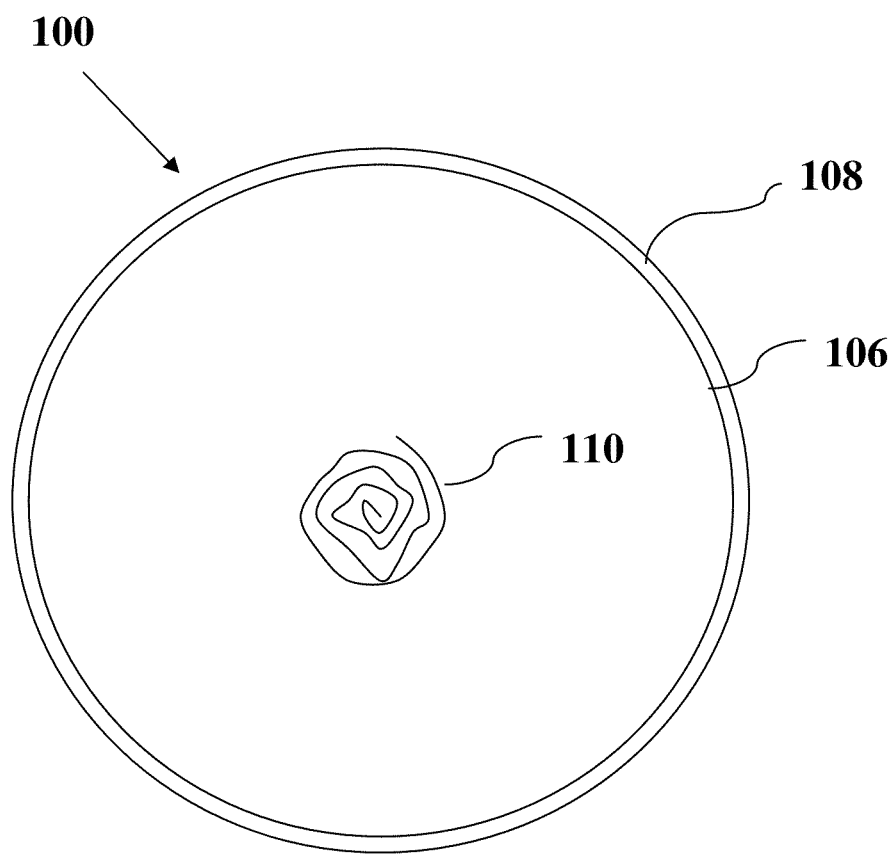

Reference is made to FIGS. 4A and 4B, which schematically illustrate a partially sectioned perspective view and a cross-sectional view, respectively, of examining device 100 according to another embodiment of the present invention. Plugs 102 and 104 and device body 106 encapsulate monitoring mechanism 110. In FIGS. 4A and 4B, monitoring mechanism 110 is shaped as a thin sheet, scrolled or bunched to fit into a pocket formed by plugs 102 and 104 and device body 106. Other configurations or arrangements of monitoring mechanism 110 may be used.

Figure 5A:
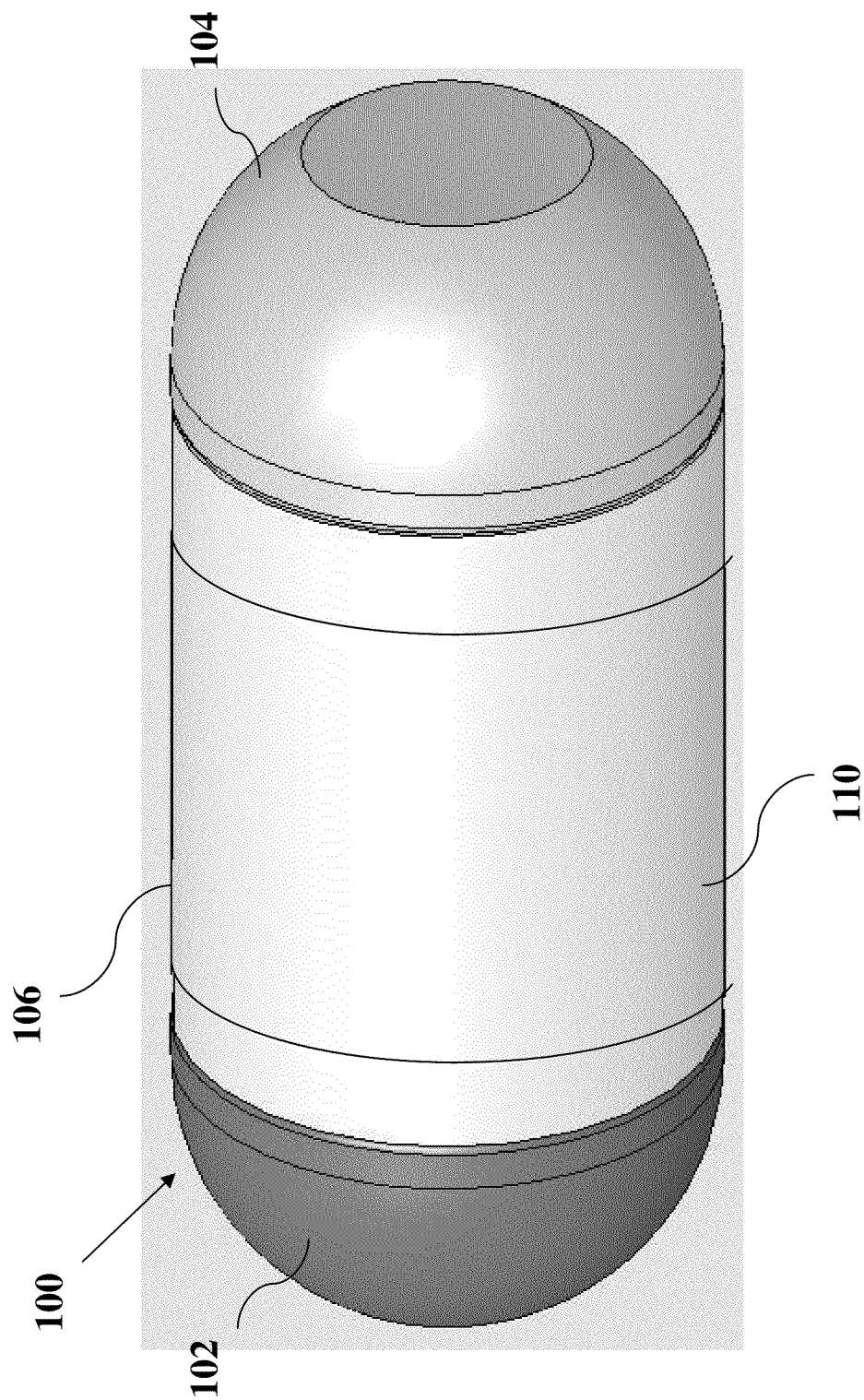
FIGS. 5A and 5B are schematic illustrations of a perspective view and a cross-sectional view, respectively, of an in-vivo examining device according to an embodiment of the present invention.
Figure 5B:
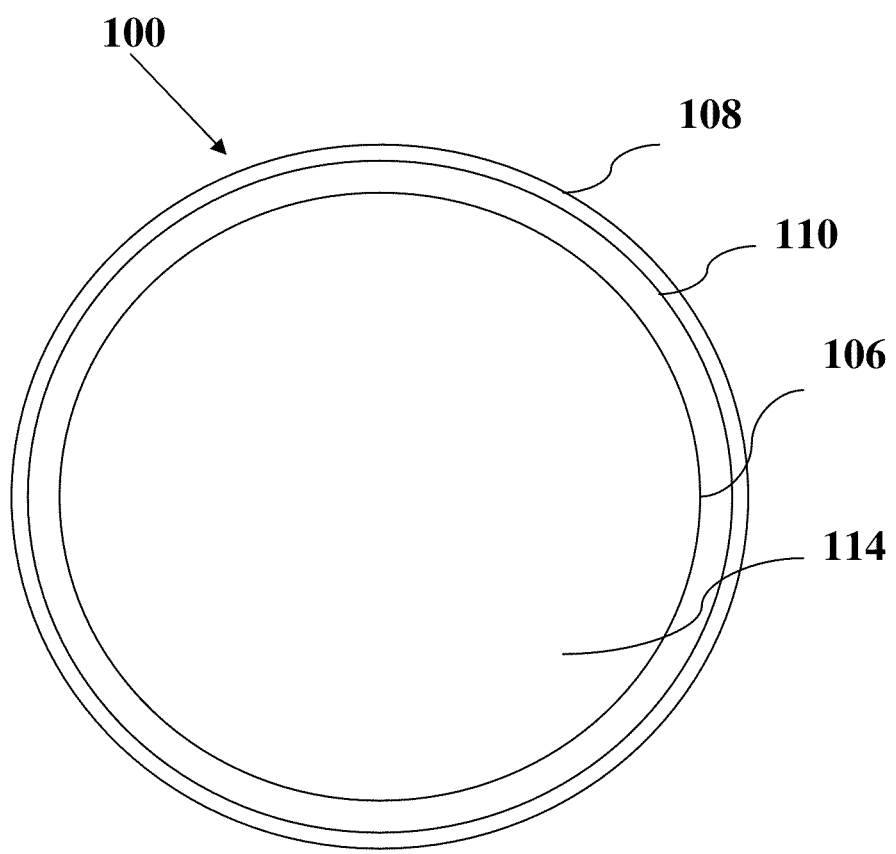

Reference is made to FIGS. 5A and 5B, which schematically illustrate a perspective view and a cross-sectional view, respectively, of the examining device 100 according to another embodiment of the present invention. Monitoring mechanism 110 may be composed of a flat RFID tag sheet wrapped around device body 106 to form a cylindrical shape, as shown in FIG. 5A. Monitoring mechanism 110 may be positioned between device body 106 and coating 108, as shown in FIG. 5B. Coating 108 is not illustrated in FIG. 5A so as not to obscure the view of other components. Other configurations or arrangements of monitoring mechanism 110 may be used.

Compared to embodiments described in reference to FIGS. 3, 4A and 4B, in the embodiment described in reference to FIGS. 5A and 5B, a greater amount of device body 106 may be have to be degraded in order to expose monitoring mechanism 110 to in-vivo fluids entering through openings 112, since monitoring mechanism 110 is peripheral to device body 106. In one embodiment, the material of device body 106 degrades relatively quickly so that, as compared to the aforementioned embodiments, the additional amount of material of device body 106 to degrade will not significantly affect the critical period (e.g., approximately 13 hours) for testing the activity of monitoring mechanism 110. In another embodiment, a different critical period may be used (e.g., 13½ or 14 hours).

In other embodiments, monitoring mechanism 110 may be positioned between device body 106 and coating 108 while further being in contact with plugs 102 and 104. In one embodiment, monitoring mechanism 101 may be composed of a flat RFID tag sheet wrapped around device body 106 to form a cylindrical shape of the same length as the length of device body 106 such that it may be in contact with plugs 102 and 104. Accordingly, when one of plugs 102 and 104 degrades, monitoring mechanism 101 may be exposed to in-vivo fluids and thus be deactivated. In one embodiment, monitoring mechanism 101 may be deactivated by exposure to in-vivo fluids through the plugs 102 and 104 prior to being exposed through device body 106.

Figure 6A:
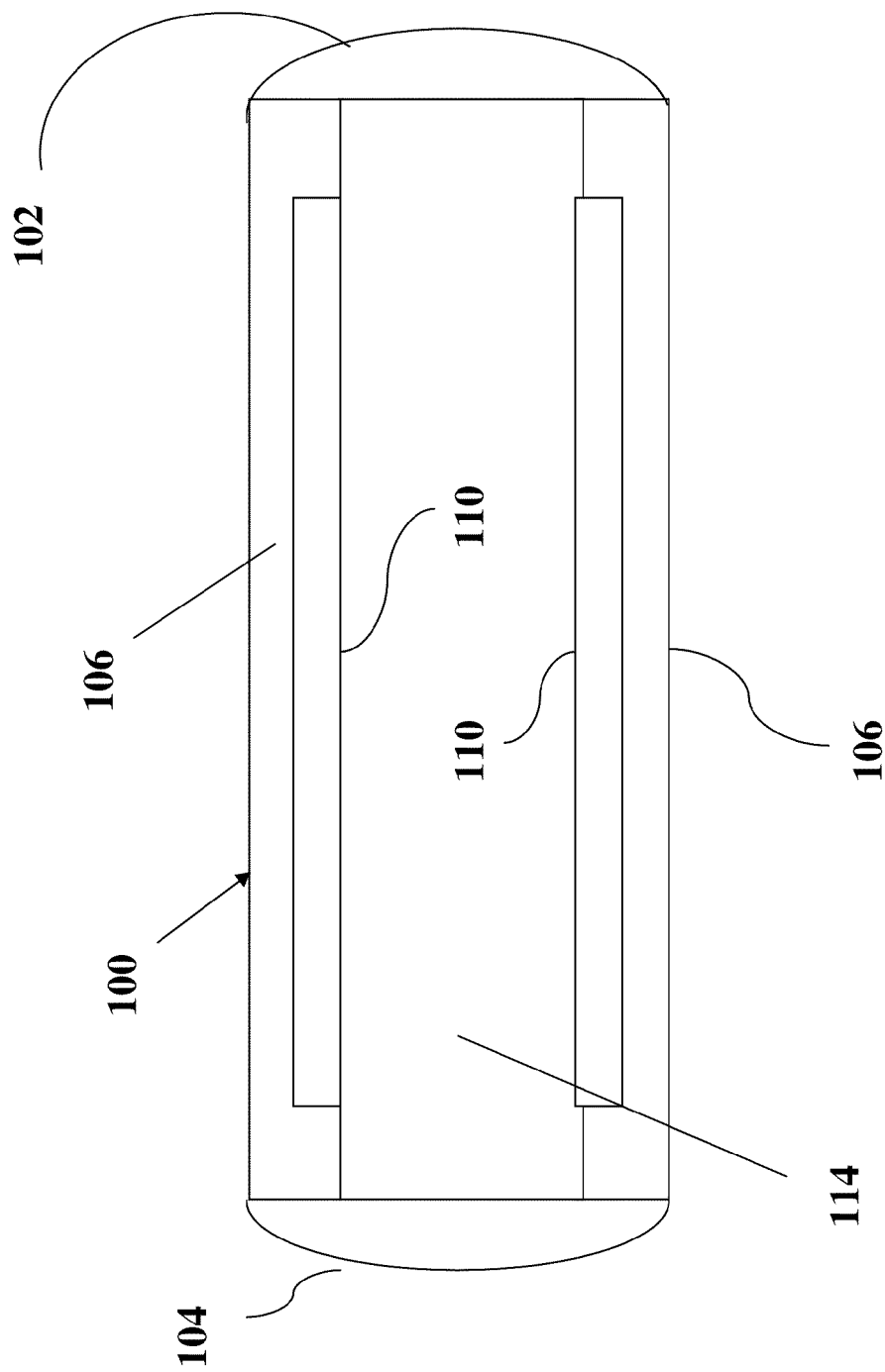
FIGS. 6A and 6B are schematic illustrations of cross-sectional views of an in-vivo examining device taken along a longitudinal axis and a lateral axis thereof, respectively, according to an embodiment of the present invention.
Figure 6B:
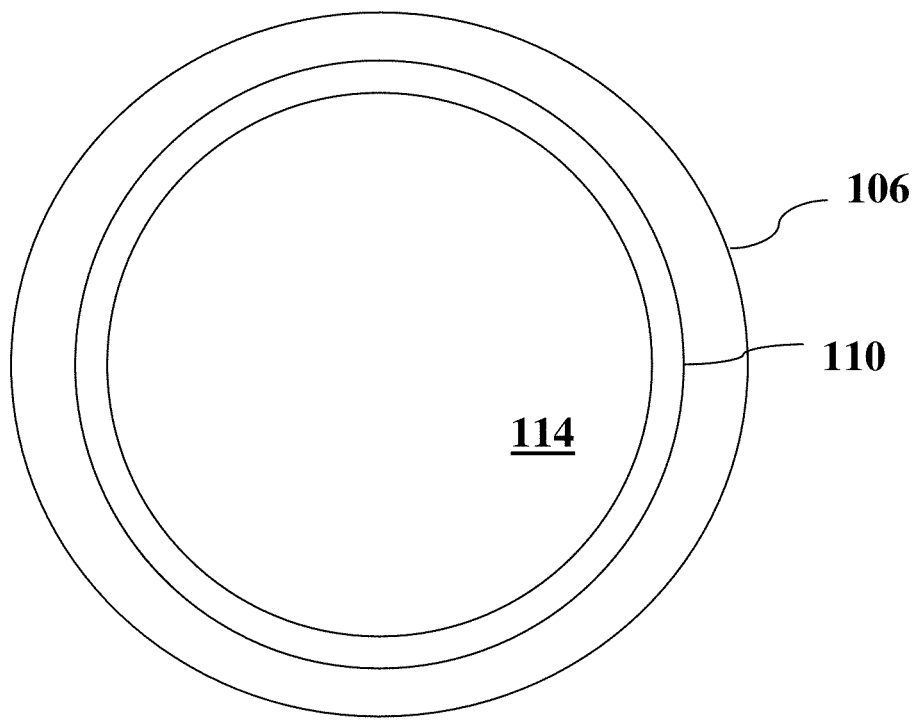

Reference is made to FIGS. 6A and 6B, which schematically illustrate cross-sectional views of examining device 100 taken along a longitudinal axis and a lateral axis thereof, respectively, according to another embodiment of the present invention. Monitoring mechanism 110 may be formed within degradable device body 106. For example, monitoring mechanism 110 may be wrapped around filler material 114, which may in turn be wrapped by another layer of degradable material 106. Materials 106 and 114 may be composed of different degradable materials having different rates of degrading that depend on the in-vivo substances (e.g., fluids, enzymes, bacteria, etc.) associated with different regions of body lumen 101 in which device 100 is located. Material 106 may be composed of a material that degrades when exposed to in-vivo substances associated with the colon, while material 114 may be composed of a material that degrades when exposed to in-vivo substances associated with the small bowel. For example, materials 114 and 106 may be similar to materials described in reference to plugs 102 and 104, respectively.

Degradable material 106 surrounding monitoring mechanism 110 may have a higher rate of degrading than the filler material 114. Therefore, once exposed to degrading in-vivo substances, degradable material 106 will be degraded, thereby exposing monitoring mechanism 110 underneath, which may be degraded from an exterior surface thereof. Alternatively, degradable filler material 114 may have a higher rate of degrading than the layer of degradable material 106 surrounding monitoring mechanism 110. Therefore, once exposed to in-vivo substances, filler material 114 will degrade, such that monitoring mechanism 110 may be exposed to in-vivo substances along an internal surface thereof bordering degradable filler material 114 and may be degraded from an interior or center-most surface thereof. In some embodiments of the present invention, an effervescent component may be added to degradable material 114 to expedite the depletion of degradable material 114.

In some embodiments, a thin layer of degradable material 106 may surround monitoring mechanism 101 so as to create a thin wall cylinder. If filler material 114 degrades prior to degradable material 106 (i.e., device 100 is stuck in the small bowel), the thin layered cylinder composed of degradable material 106 would collapse, thereby ensuring that device 100 safely passes the small bowel. If degradable material 106 degrades prior to filler material 114, i.e., device 100 has reached the colon, then filler material 114 may either safely pass through the colon in its initial dimensions or may be degraded in the colon so as to have a significantly smaller dimension of width or girth so as to safely pass through the colon (although the degradation may be at a lower rate of degrading than in the small bowel).

Figure 7B:
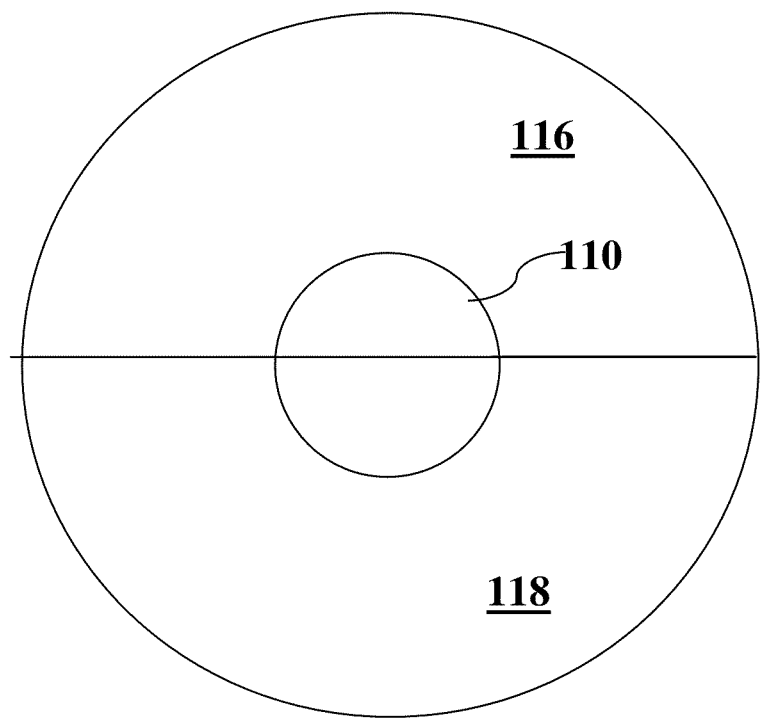

Reference is made to FIGS. 7A and 7B, which schematically illustrate cross-sectional views of an in-vivo examining device 100 taken along a longitudinal axis and a lateral axis thereof, respectively, according to an embodiment of the present invention. Device 100 includes two or more degradable material regions 116 and 118, e.g., formed as semi-cylinders. Regions 116 and 118 may be composed of different degradable materials having different rates of degrading that depend on the in-vivo substances (e.g., fluids, enzymes, bacteria, etc.) associated with different regions of body lumen 101 in which device 100 is located. For example, region 116 may degrade when exposed to in-vivo substances associated with the small bowel, while region 118 may degrade when exposed to in-vivo substances associated with the colon. Regions 116 and 118 may be similar to materials described in reference to plugs 102 and 104, respectively.

Regions 116 and 118 may protect monitoring mechanism 110 from exposure to in-vivo fluids and substances of body lumen 101. According to embodiments of the invention, regions 116 and 118 may degrade at different times depending on the region of body lumen 101 in which device 100 is located, thereby exposing monitoring mechanism 110. In some embodiments, semi-cylinders 116 and 118 are positioned along device 100 such that one of their ends meets one of device 100's ends and the other of their other ends meets the other end of device 100. In such embodiments, regardless of which end of device 100 is leading or trailing as device 100 traverses body lumen 101, at least one end will receive a maximal amount of exposure to in-vivo fluids and thus either region 116 or region 118 may degrade depending on the region of body lumen 101 in which device 100 is located.

In various embodiments, monitoring mechanism 110 may be flat, curved, cylindrical, rolled, folded, threaded, twisted or otherwise configured. In various embodiments, monitoring mechanism 110 may be positioned inside, outside, adjacent to, spaced from, traversing, crossing, wrapped abound, or surrounded by, aligned with, etc., component(s) of device 100 including, for example, plugs 102 and 104, device body 106, degradable material 114, covering 108, openings 112.

In the aforementioned embodiments, device 100 is described to have multiple layers or regions of different degradable materials. For example, in the embodiments of FIGS. 2, 3, 4A and 5A, dissolvable plugs 102 and 104 may be located at opposite ends of device 100. In the embodiments of FIGS. 7A and 7B, regions 116 and 118 are cylindrical halves of device 100. In another embodiment, multiple layers of material may be nested to encapsulate each other as a series of successive barriers. In yet another embodiment, device body 106 may be composed of nested cylinders of material concentric about a longitudinal axis of the capsule. Any other arrangement of layers may be used. Each layer may be composed of the same or a different material and may have the same or a different rate of degrading and/or pH level(s) at which the material degrades.

In one embodiment of the invention, multiple monitoring mechanisms 110 may be used. Each monitoring mechanisms 110 may have a unique RFID pattern that generates a unique and distinguishable identification signal. Each monitoring mechanisms 110 may be protected by a separate one of degradable plugs 102 and 104 or regions 116 and 118. Each of plugs 102 and 104 or regions 116 and 118 degrades by in-vivo substances in a specific region of body lumen 101. When device 100 is initially ingested, i.e., before degrading, signals are received at an external receiver from each of the multiple monitoring mechanisms 110. When each plug 102 and 104 or region 116 and 118 degrades, the monitoring mechanism 110 individually protected thereby is exposed to in vivo fluids and is itself degraded and, thereby, inactivated, such that no signals are transmitted therefrom.

Signals from device 100 may be monitored to determine which monitoring mechanism 110 is no longer transmitting signals. The specific monitoring mechanism 110 that is no longer transmitting signals indicates that the adjacent plug 102 or 104 or surrounding material 116 or 118 has degraded. Since each of plugs 102 and 104 or regions 116 and 118 degrades by in-vivo substances in a specific region of body lumen 101, the region in which device 100 can be located is determined. In one embodiment, based on transmitting signals, it may be determined whether device 100 has passed to the colon or alternatively whether device 100 is stuck in the small bowel.

In one example, device 100 may have multiple indistinguishable monitoring mechanisms 110. In this embodiment, the number of signals or the signal strength may be used to determine amounts of material that have and/or have not been degraded. In one embodiment, miniature RFID tags, e.g., "RFID powder" (e.g., "contactless powder IC chip" by Hitachi, whose dimensions are 0.05*0.05 mm2, 0.005 mm thick, as detailed at http://www.hitachi.com/rd/pdf/news/cr1070213nrde_RFID.pdf) may be spread and/or homogenously embedded throughout one or more dissolvable layers of material of device 100. In this example, when a portion of plug 102 and 104 or regions 116 and 118 degrades, a percentage of signal or signal strength remaining may correspond to a percentage of the remaining dissolvable capsule material. In an embodiment of the invention, if device 100 traveling through a patient with initial dimensions (corresponding to signals from in monitoring mechanisms 110) is stuck at a location in the GI tract for a period of time, after which, upon degrading to have a relatively smaller dimension of width, it is freed, in-vivo capsules may be individualized for the patient to have a dimension of width not larger than the relatively smaller dimension of width.

In another embodiment, a single plug may replace plugs 102 and 104. For example, such a plug may degrade at a first rate when exposed to in-vivo substances in the small bowel (e.g., to expose monitoring mechanism 110 in approximately 24 hours) and may degrade at a second rate when exposed to in-vivo substances in the colon (e.g., to expose monitoring mechanism 110 in approximately 1 hour from entering the colon), e.g., the second rate being faster than the first rate. Therefore, in this embodiment, if device 100 passes unobstructed to the colon, monitoring mechanism 110 should stop transmitting signals after "degradation time of an unobstructed passage", e.g. approximately 13 hours. However, in this embodiment, if device 100 is retained in the small bowel, monitoring mechanism 110 will continue to transmit signals after approximately 13 hours. For example, such a single plug may be composed of a mixture or striation of the materials used for plugs 102 and 104. In another embodiment, two duplicate plugs having this dual rate property, may be disposed at opposite ends of device 100 so that, regardless of which plug is leading or trailing as device 100 traverses body lumen 101, at least one plug will receive a maximal amount of exposure to in-vivo fluids.

Examining device 100 may be used to simulate the passage of another in-vivo device, such as a diagnostic and/or therapeutic device, through a body lumen, for example, an autonomous diagnostic and/or therapeutic device. In this case, obtaining information on the passage of the examining device through the body lumen may be advantageous in designing a specific in-vivo device or in determining whether a certain in-vivo device may be safely used on a patient. In one embodiment, different sized and shaped examining devices 100 according to an embodiment of the invention may be passed through a body lumen to determine the most suitable size and shape for an in-vivo device to be freely and safely passed through the same lumen.

In one embodiment of the present invention, the initial dimensions of device 100 may be typically determined in accordance with the known anatomy and/or physiology of a body lumen. In its final phase, the dimensions of the examining device may be typically substantially smaller and its shape possibly changed such that it may freely pass through the body lumen even if the lumen dimensions may be smaller than expected in accordance with the known anatomy and/or physiology of the body lumen. For example, if the final dimensions of device 100 are of the same scale as the dimensions of monitoring mechanism 110, e.g., a diameter of about 2.5 mm (with or without coating 108 which may be pliable after the plugs and the filler have dissolved), it is ensured that device 100 will freely pass through the GI tract, specifically through strictures in the small bowel, if any. Proceeding from initial dimensions to final dimensions, device 100, may, for example, be promoted by endo-luminal conditions or may be externally controlled.

Passing device 100 through body lumen 101 may, for example, simulate the passage of a target in-vivo device through that body lumen, and thus a safe method of indication may be provided as to the transferability of the target in-vivo device in the body lumen.

In one embodiment of the present invention, device 100 may include an examining mechanism, such as a thermometer, pH meter, etc., for examining endo-luminal conditions, or other sensing devices such as an imaging device. In another embodiment of the present invention, device body 106 may contain one or more medical drugs, for example, that may be released, for example in an abnormally configured lumen during depletion of degradable material 114.

Figure 8A:
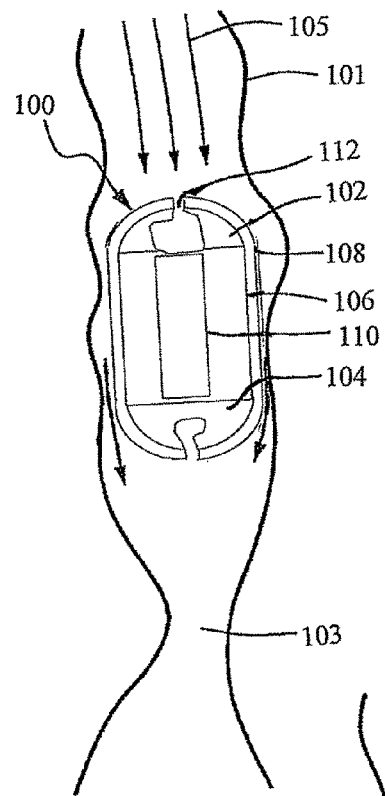
FIGS. 8A, 8B and 8C are schematic illustrations of a progression of the examining device passing through a stricture of a body lumen according to an embodiment of the present invention.
Figure 8B:
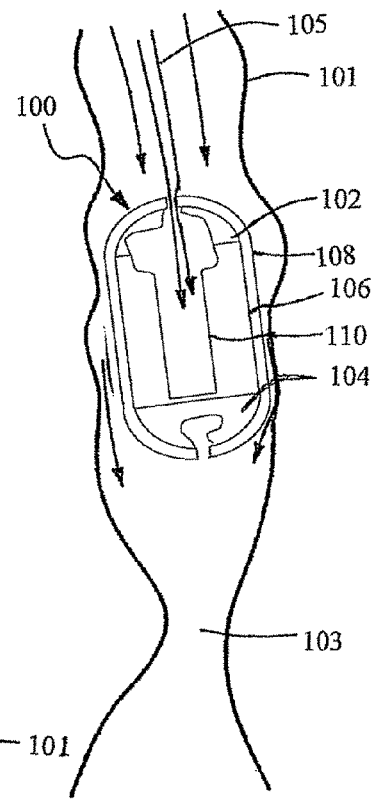
Figure 8C:
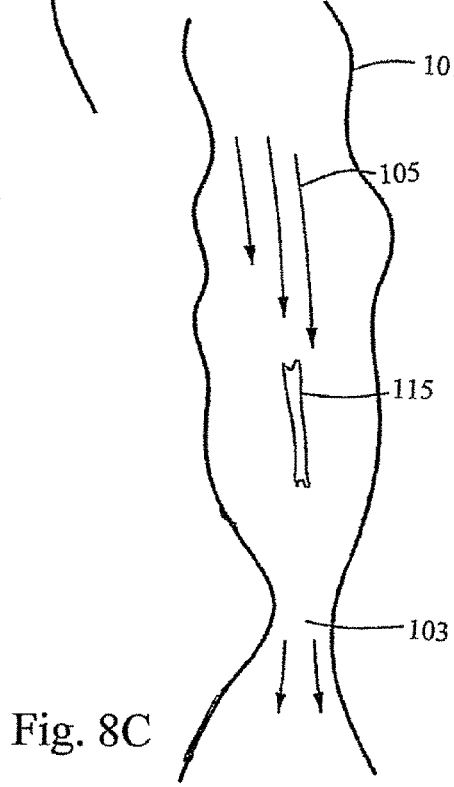

Reference is now made to FIGS. 8A, 8B and 8C showing consecutive schematic illustrations of a progression of examining device 100 passing through stricture 103 of body lumen 101 according to an embodiment of the present invention.

FIG. 8A shows a lengthwise cross sectional schematic illustration of device 100 traveling through body lumen 101 in the direction of the arrows and approaching an area with stricture 103. During travel through body lumen 101, contact of device 100 with in-vivo fluids 105 through openings 112 may degrade plugs 102 and 104. For a predetermined period of time, the degrading of plugs 102 and 104 and/or the omnidirectional depletion of device 100 may continue without compromising the rigidity or substantially altering the outer dimensions of width of device 100.

The rate at which plugs 102 and 104 degrade may be a function of the type of in-vivo substance to which plugs 102 and 104 are exposed and, thus, may be a function of the region of body lumen 101 (each region composed of different in-vivo substances) in which device 100 is located. For example, within the small bowel, plug 102 may degrade at a faster rate than plug 104. However, if device 100 progresses substantially unobstructed to the colon, the overall rate at which plug 104 degrades the colon may be faster than the rate at which plug 102 would degrade if device 100 were stuck in the small bowel. In one embodiment of the invention, from the time of ingestion of device 100 into a patient's body, the earliest time that either of plugs 102 and 104 may degrade occurs when the capsule passes unobstructed to the colon. In one example, the rate at which one of plugs 102 and 104 degrades increases is a function of progression through body lumen 101.

When one or both of plugs 102 and 104 degrade, monitoring mechanism 110 (e.g., which is composed of a degradable material) may be exposed to in-vivo fluids and will stop transmitting identification signals. Since plugs 102 and 104 degrade at different rates based on the region of body lumen 101 in which device 100 is located, monitoring mechanism 110 will stop transmitting identification signals at corresponding different times, depending on whether plug 102 or 104 degrades first. Accordingly, the absence of a signal from monitoring mechanism 110 at one of the corresponding different times may indicate the region of body lumen 101 in which device 100 is located.

For example, if stricture 103 in a first in-vivo environment (e.g., the small bowel) is sufficiently narrow and rigid as to prevent the passage of device 100, plug 102 typically degrades at a faster rate than plug 104 so that monitoring mechanism 110 stops transmitting signals after "degradation time of an obstructed passage", e.g. within 40 hours. However, if stricture 103 (e.g., in the small bowel) is sufficiently wide to allow the unobstructed passage of device 100 to a second in-vivo environment (e.g., the colon), the rate at which plug 104 degrades after an additional time in the second in-vivo environment is increased so that monitoring mechanism 110 stops transmitting signals after "degradation time of an unobstructed passage", e.g., within 1 hour from entering the colon or up to 13 hours from ingestion. Typically, the "degradation time of an unobstructed passage" will be significantly shorter than the "degradation time of an obstructed passage". In this way, an external receiving device may scan for signals from monitoring mechanism 110 during a time period after the "degradation time of an unobstructed passage" but before the "degradation time of an obstructed passage" in order to determine whether on not device 100 has passed to the second in-vivo environment (i.e., if signals are not transmitted and if signals continue to be transmitted, respectively).

In some embodiments of the present invention, the erosion of plugs 102 and 104 may be a function of the degree of contact plugs 102 and 104 may have with the surrounding in-vivo fluids. For example, the orientation of device 100 with respect to the body lumen may result in one of its plugs, for example plug 102, having greater exposure to in-vivo fluids as compared to another of its plug 104. For example, plug 102, which is facing an upstream direction, may have more exposure to in-vivo fluids as compared to plug 104, which is facing in a downstream direction. As such, the one of plugs 102 and 104 that is facing in the upstream direction may erode at a faster rate than it would if it were facing the downstream direction. Accordingly, the aforementioned rates at which each of plugs 102 and 104 degrades may be approximate and variable depending on the orientation of the omnidirectional capsule as it traverses body lumen 101. These rates may be calculated as averages of the rates that each plug is expected to degrade if it were oriented in the leading or tailing direction.

In the view of FIG. 8B, plug 104 is depicted as having degraded by an amount sufficient to expose monitoring mechanism 110 to in-vivo fluids, while plug 102 has not. In a first demonstrative example, as shown in FIG. 8B, plug 104 is adapted to degrade before plug 102 when device 100 passes unobstructed by stricture 103 to the second in-vivo environment (e.g., the colon). Plug 104 is adapted to degrade in the second in-vivo environment after the lapse of "degradation time of an unobstructed passage", which is typically shorter than a predetermined "degradation time of an obstructed passage". Since an external receiving device typically scans for signals from monitoring mechanism 110 after the "degradation time of an unobstructed passage", the external receiver device will not receive signals from monitoring mechanism 110. Accordingly, it may be determined that device 100 has passed stricture 103 unobstructed to the second in-vivo environment (e.g., the colon).

In an alternative demonstrative example, plug 102 is adapted to degrade before plug 104 when device 100 is obstructed by stricture 103 in the first in-vivo environment (e.g., the small bowel). Plug 102 is adapted to degrade in the first in-vivo environment after the lapse of "degradation time of an obstructed passage, which is typically longer than a predetermined "degradation time of an unobstructed passage". Since an external receiving device typically scans for signals from monitoring mechanism 110 after the "unobstructed" time period and before the "obstructed" time period (before the view shown in FIG. 8B), the external receiver device will continue to receive signals from monitoring mechanism 110. Accordingly, it may be determined that device 100 is obstructed by stricture 103 in the first in-vivo environment (e.g., the small bowel).

Once monitoring mechanism 110 has been deactivated, if the time of deactivation is before or after the obstructed time period, it may be determined that a non-degradable medical device with a dimension of width substantially equal to that of device 100 may or may not pass, respectively, substantially unobstructed through a designated narrow region body lumen 101 (e.g., the small bowel).

Before and during the time that monitoring mechanism 110 is deactivated (e.g., in FIGS. 8A and 8B), although some dimensions of structures of device 100 may be altered or reduced, the outer dimension of device 100, i.e., the width/girth or diameter of device 100, may be substantially constant. It is this dimension, the width or girth of device 100 relative to the opening of body lumen 101, which generally determines the passage of the device 100. Thus, the dimension of width or girth of device 100 is preferably preserved until after the determination of passage is made (e.g., once the patient is scanned in order to find out if the monitoring mechanism 110 has been deactivated). This is accomplished since, compared to the rate of degrading of monitoring mechanism 110 (e.g., quickly or instantly), the rate of degrading of device body 106 to collapse the device 100 walls (e.g., coating 108) is relatively slower.

After it is determined that device 100 with outer dimension of width or girth may pass the relatively narrow region, e.g., the small bowel, it may be inferred that a device with substantially the same outer dimension of width or girth will also pass regions that are wide relative to the narrow region. The analysis may be considered complete at this stage. Device 100 is designed so that the degrading of material within device 100 may advance, and non-degradable coating 108 may collapse to reduce the width of device 100 to form collapsed device 115, as shown in FIG. 8C. Alternatively, or additionally, a patient may drink a solvent or other material to hasten the degradation of device 100. Collapsed device 115 (e.g., composed only of non-degradable coating 108, as all other structures in this embodiment have degraded) may then easily pass the remainder of the patient's gastrointestinal tract until it is excreted from the body. Since plugs 102 and 104 degrade at different rates depending on the in-vivo environment to which device 100 has progressed, any further degrading of device 100, e.g., the erosion of device body 106 sufficient to collapse coating 108, may likewise depend on the in-vivo environment to which device 100 progresses.

A health professional may monitor (e.g., with known monitoring devices) the passage of device 100 through a body lumen to determine the presence of abnormal body lumen configurations, e.g., strictures and constrictions due to tumors, polyps, infection etc. The absence of signals from monitoring mechanism 110 between a predetermined "unobstructed" and "obstructed" time periods may be an indication that no strictures were encountered during passage through the body lumen, e.g., the GI tract. Detection of signals from monitoring mechanism 110 between a predetermined "unobstructed" and "obstructed" time periods may be indication that abnormal body lumen configurations were encountered. In some embodiments of the present invention, the predetermined time periods may be in the order of 13 to 24 hours. In other embodiments, periods of approximately 15 to 20 hours may be used. In still alternate embodiments, other time limits may be used, and examining devices for other body lumens may be designed in accordance with the specific body lumen having specific and known anatomy and physiology.

Figure 9:
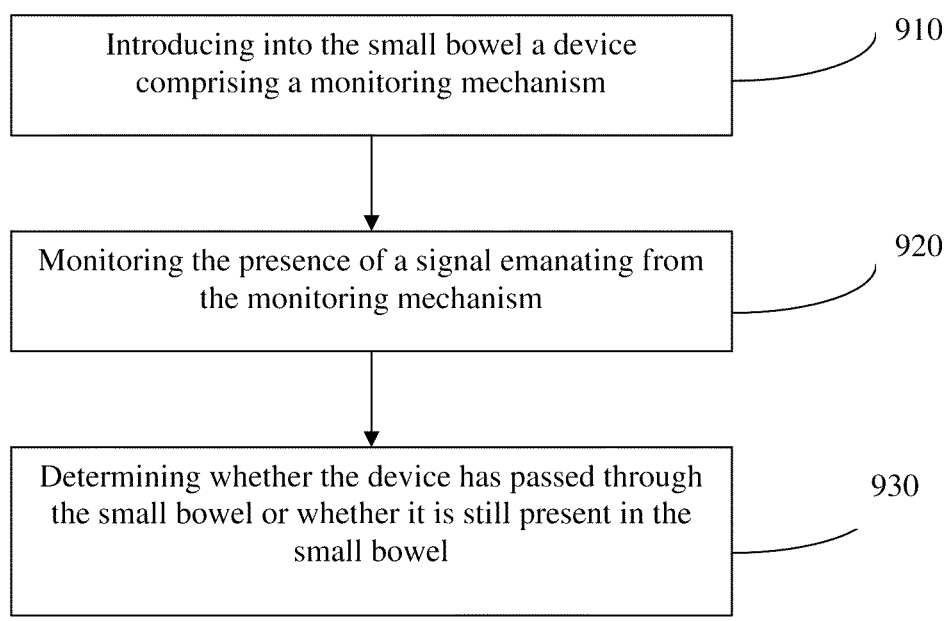
FIG. 9 is a flow-chart illustrating a method for examining a body lumen according to an embodiment of the present invention.

Reference is now made to FIG. 9, which is a flow-chart illustrating a method for examining a body lumen according to an embodiment of the present invention. The method according to FIG. 9 may be a method for determining the presence of a stricture in a small bowel. The method may comprise the step 910 of introducing into the small bowel a device that includes a dissolvable portion for dissolving in the colon at a first rate and for dissolving in the small bowel at a second slow rate. According to some embodiments, the first rate is slower than the second rate. The device may further include a monitoring mechanism. The device body may be covered by an impermeable coating defining at least two openings on opposite sides of the device body. According to some embodiments, the device may be introduced into the patient's small bowel by ingestion or by placement with an in-vivo device, e.g. an endoscope or other in-vivo delivery devices it may be attached to. The method may further comprise the step 920 of monitoring the presence of a signal emanating from the monitoring mechanism by, for example, scanning the patient with an external scanner after a predetermined time period, e.g., after "degradation time of an unobstructed passage" in order to detect a signal, e.g., an RFID signal, emanating from the monitoring mechanism. The method may comprise the step 930 of determining whether the device has passed through the small bowel or whether it is still present within the small bowel due to for example, strictures in the small bowel.

According to some embodiments, after the monitoring mechanism is exposed to in-vivo fluids (whether they are in-vivo fluids native to the small bowel or the colon), the step of monitoring the device may comprise detecting no signal is emanated from the monitoring device. According to the time period that has passed until the detection of no signal emanated from the monitoring mechanism, it may be determined whether the device has freely passed through the small bowel or whether it was stuck in the small bowel. If no signal is detected after 6 to 13 hours, it may be determined that the device has freely passed through the small bowel, since those are time periods which correlate to a normal transit time of a device through the small bowel. If no signal is emanated after a longer period of time, it may be determined that the device has been stuck in the small bowel and thus it may identify presence of strictures in the small bowel.

In some embodiments, after a predetermined time period, the device body and at least the dissolvable body are dissolved. According to some embodiments, the predetermined time period is a period of between 6 hours and 24 hours. Other time periods may be suitable, all according to the composition of the device, the density of the composition, the size of the openings that expose the device to in-vivo fluids, etc.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. An in-vivo examining device to identify the presence of strictures in the small bowel comprising:
   a monitoring mechanism configured to be deactivated upon exposure to in-vivo substances native to the small bowel or the colon; and
   a degradable device body comprising at least a first body portion configured to degrade at a first rate when exposed to in-vivo substances native to the small bowel and at a second rate when exposed to in-vivo substances native to the colon, said first rate being slower than said second rate,
   wherein degradation of said degradable device body exposes said monitoring mechanism to substances native to the small bowel or the colon.

2. The device according to claim 1, further comprising a non-degradable or slowly-degradable coating surrounding said degradable device body, wherein said coating comprises at least one opening.

3. The device according to claim 2, wherein said coating includes parylene C.

4. The device according to claim 1, wherein the monitoring mechanism is a radio-frequency identification (RFID) tag.

5. The device according to claim 1, wherein the monitoring mechanism is composed of a material selected from the group consisting of: paper, degradable plastic and degradable rubber.

6. The device according to according to claim 1, wherein said RFID tag is rolled around itself within the device body.

7. The device according to according to claim 1, wherein said RFID tag is wrapped around the device body and covered by coating.

8. The device according to according to claim 2, wherein said device body comprises filler disposed within said coating, the filler being dissolvable in in-vivo fluids.

9. The device according to according to claim 1, wherein said device body further comprises a second body portion which is configured to degrade at a third rate when exposed to in-vivo substances native to the small bowel and at a fourth rate when exposed to in-vivo substances native to the colon, said first rate being slower than said second rate,
wherein said first and second portions are positioned at opposite sides along the longitudinal axis of said device.

10. An in-vivo examining device to identify the presence of strictures in the small bowel comprising:
a monitoring mechanism configured to be deactivated upon exposure to in-vivo substances native to the small bowel or the colon; and
a degradable device body comprising a first body portion configured to degrade at a first rate when exposed to in-vivo substances native to the small bowel and a second body portion which degrades at a second rate when exposed to in-vivo substances native to the colon, said first rate being slower than said second rate,
wherein degradation of said degradable device body exposes said monitoring mechanism to substances native to the small bowel or the colon.

11. The device according to claim 10, wherein said first body portion and said second body portions are plugs positioned at opposite sides along the longitudinal axis of said device.

12. The device according to claim 10, wherein the first body portion comprises a material selected from the group consisting of: Glyceryl dibehenate, microcrystalline cellulose, Lactose anhydr., and PVP K-90.

13. The device according to claim 10, wherein the second body portion comprises a material selected from the group consisting of: Crosslinked guar, a-Galactosidase, b-Mannanase, biodegradable polysaccharides, guar gum hydrogel, Trisodium trimetaphosophate, Pectin, Polysaccharide, and Calcium pectinate.

14. A method for determining the presence of a stricture in a small bowel, said method comprising:
introducing an in-vivo examining device into the small bowel, said device comprising:
a dissolvable portion configured to dissolve at a first rate when exposed to in-vivo substances native to the small bowel and at a second rate when exposed to in-vivo substances native to the colon, said first rate being slower than said second rate, and
a monitoring mechanism, and
a device body covered by an impermeable coating defining at least two openings on opposite sides of the device body;
monitoring the presence of a signal emanating from the monitoring mechanism; and
determining, based on said monitoring, whether said device has passed through the small bowel thus indicating the absence of a stricture in the small bowel or whether the device is still present within the small bowel thus indicating the presence of a stricture in the small bowel.

15. The method according to claim 14, wherein the step of introducing the device comprises ingesting the device.

16. The method according to claim 14, wherein the step of monitoring the device comprises detecting a signal emanated from said monitoring device.

17. The method according to claim 14, wherein, after said monitoring device is exposed to in-vivo fluids, the step of monitoring the device comprises detecting no signal emanated from the monitoring device.

18. The method according to claim 14, wherein, after a predetermined period, the device body and at least the dissolvable portion are dissolved.

19. The method according to claim 18, wherein the predetermined time period is a period of between 6 hours and 24 hours.

20. A system for determining the presence of strictures in the small bowel, the system comprising:
an examining device, said device including a first dissolvable portion configured to dissolve at a first rate when exposed to in-vivo substances in the small bowel and a second dissolvable portion configured to dissolve at a second rate when exposed to in-vivo substances in the colon, said first rate being slower than said second rate, and a monitoring mechanism disposed between the first and second dissolvable portions, said device body covered by an impermeable coating defining at least two openings on opposite sides of the device body; and
a receiver configured to detect a signal emanating from said monitoring mechanism after a predetermined time period to determine the presence of said examination device within the small bowel.

* * * * *